(12) United States Patent
Hansen et al.

(10) Patent No.: US 10,000,782 B2
(45) Date of Patent: Jun. 19, 2018

(54) RECOMBINANT HOST CELL FOR THE BIOSYNTHESIS OF VANILLIN OR VANILLIN BETA-D-GLUCOSIDE

(71) Applicant: International Flavors & Fragrances Inc., New York, NY (US)

(72) Inventors: Esben Halkjaer Hansen, Frederiksberg C (DK); Swee Chuang Lim Hallwyl, Vallensbaek Strand (DK); Klavs Riishede Hansen, Koebenhavn S (DK)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 56 days.

(21) Appl. No.: 14/905,228

(22) PCT Filed: Jul. 11, 2014

(86) PCT No.: PCT/US2014/046315
§ 371 (c)(1),
(2) Date: Jan. 14, 2016

(87) PCT Pub. No.: WO2015/009558
PCT Pub. Date: Jan. 22, 2015

(65) Prior Publication Data
US 2016/0153016 A1 Jun. 2, 2016

Related U.S. Application Data

(60) Provisional application No. 61/846,658, filed on Jul. 16, 2013.

(51) Int. Cl.
| | | |
|---|---|---|
| *C12P 19/46* | (2006.01) | |
| *C12P 7/24* | (2006.01) | |
| *C07C 47/58* | (2006.01) | |
| *C07H 15/203* | (2006.01) | |
| *C12N 9/04* | (2006.01) | |
| *C12N 15/70* | (2006.01) | |
| *C12N 15/81* | (2006.01) | |
| *C12N 15/82* | (2006.01) | |

(52) U.S. Cl.
CPC .............. *C12P 19/46* (2013.01); *C07C 47/58* (2013.01); *C07H 15/203* (2013.01); *C12N 9/0006* (2013.01); *C12N 15/70* (2013.01); *C12N 15/81* (2013.01); *C12N 15/815* (2013.01); *C12N 15/8257* (2013.01); *C12P 7/24* (2013.01); *C12Y 101/01001* (2013.01)

(58) Field of Classification Search
CPC .......... C12P 7/24; C12P 19/46; C12N 9/0006; C12N 15/8257; C12N 15/815; C12N 15/81; C12N 15/70; C12Y 101/01001; C07H 15/203; C07C 47/58
See application file for complete search history.

(56) References Cited

U.S. PATENT DOCUMENTS

| | | | |
|---|---|---|---|
| 6,372,461 B1 | 4/2002 | Frost | 435/156 |
| 2007/0231864 A1 | 10/2007 | Havkin-Frenkel et al. | |
| 2014/0245496 A1 | 8/2014 | Hansen et al. | 800/298 |

FOREIGN PATENT DOCUMENTS

WO   WO2013022881   2/2013

OTHER PUBLICATIONS

Zhou et al., Cell Mol Life Sci 63(19-20):2260-2290, 2006.*
Kozak, M., Gene 234:187-208, 1999.*
Liénard et al., Recombinant Proteins from Plants, Methods in Molecular Biology, Faye L., Gomord V. (eds), vol. 483, pp. 135-144, 2009.*
Brochado et al. "Improved vanillin production in baker's yeast through in silico design" Microbial Cell Factories, Biomed Central 2010 9:84.
DiGioia et al. "Metabolic engineering of *Pseudomonas fluorescens* for the production of vanillin from ferulic acid" Journal of Biotechnology 2011 156:309-316.
International Preliminary Report on Patentability in PCT/US14/046315, dated Jan. 19, 2016, PCT.
Hansen et al. "De Novo Biosynthesis of Vanillin in Fission Yeast (*Schizosaccharomyces pombe*) and Baker's Yeast (*Saccharomyces cerevisiae*)" Applicants and Environmental Microbiology 2009 2675-2774.
Iwaki et al. "Vanillin Inhibits Translation and Induces Messenger Ribonucleoprotein (mRNP) Granule Formation in *Saccharomyces cerevisiae*: Application and Validation of High-Content, Image-Based Profiling" PLOS ONE 2013 8(4) :e61748.
Li, T. & Rosazza, J.P.N. "Biocatalytic Synthesis of Vanillin" Applied and Environmental Microbiology 2000 684-687.
Liu, Z.L. "Molecular mechanisms of yeast tolerance and in situ detoxification of lignocelluloses hydrolysates" Appl. Microbiol. Biotechnol. 2011 90:809-825.
Rao, S.R. & Ravishanka, G.A. "Review Vanilla flavor: Production by conventional and biotechnological routes" Journal of the Science of Food and Agriculture 2000 80:289-304.
Walton et al. "Molecules of Interest Vanillin" Phytochemistry 2003 63:505-515.

* cited by examiner

*Primary Examiner* — Delia Ramirez
(74) *Attorney, Agent, or Firm* — Licata & Tyrrell P.C.

(57) ABSTRACT

Recombinant microorganisms, plants, and plant cells are disclosed that have been engineered to have reduced levels or activity of one or more alcohol dehydrogenases or aldehyde reductase thereby increasing the production of vanillin or vanillin beta-D-glucoside.

23 Claims, 2 Drawing Sheets

RECOMBINANT HOST CELL FOR THE BIOSYNTHESIS OF VANILLIN OR VANILLIN BETA-D-GLUCOSIDE

This application is a U.S. National Stage Application of PCT/US2014/046315 filed Jul. 11, 2014 and claims benefit of priority to U.S. Provisional Application Ser. No. 61/846,658, filed Jul. 16, 2013, the contents of each of which is are incorporated herein by reference in their entirety.

BACKGROUND

Vanillin is one of the world's most important flavor compounds with a global market of 180 million dollars. Natural vanillin is derived from the cured seed pods of the vanilla orchid (*Vanilla planifolia*), but most of the world's vanillin is synthesized from petrochemicals or wood pulp lignins. Production of natural vanillin from the vanilla pod is a laborious and slow process, which requires hand pollination of the flowers and a 1-6 month curing process of the harvested green vanilla pods (Ramachandra & Ravishankar (2000) *J. Sci. Food Agric.* 80:289-304). Production of 1 kilogram (kg) of vanillin requires approximately 500 kg of vanilla pods, corresponding to pollination of approximately 40,000 flowers. Today only about 0.25% (40 tons out of 16,000) of vanillin sold annually originates from vanilla pods, while most of the remainder is synthesized chemically from lignin or fossil hydrocarbons, in particular guaiacol. Synthetically produced vanillin is sold for approximately $15 per kg, compared to prices of $1200-4000 per kg for natural vanillin (Walton, et al. (2003) *Phytochemistry* 63:505-515).

SUMMARY OF THE INVENTION

This invention provides a recombinant host cell having the following characteristics: the recombinant host cell produces vanillin and/or vanillin beta-D-glucoside; and the recombinant host cell has reduced production or activity of a first alcohol dehydrogenase and reduced production of one or more second alcohol dehydrogenases, one or more aldehyde reductases, or a combination thereof. In some embodiments, the first alcohol dehydrogenase is Alcohol Dehydrogenase 6 (ADH6). In another embodiment, the one or more second alcohol dehydrogenases include Alcohol Dehydrogenase 7 (ADH7), Genes de Respuesta a Estres 2 (GRE2), or an ortholog thereof. In a further embodiment, the aldehyde reductase includes Aldehyde Reductase Intermediate 1 (ARI1), Aldehyde Reductase YGL039W, or an ortholog thereof. In certain embodiments, the recombinant host cell further includes a nucleic acid encoding an AROM polypeptide, a nucleic acid encoding a catechol-O-methyltransferase (COMT) polypeptide, a nucleic acid encoding a 3-dehydroshikimate dehydratase (3DSD) polypeptide, a nucleic acid encoding an aromatic carboxylic acid reductase (ACAR) polypeptide, a nucleic acid encoding a phosphopantetheine transferase (PPTase) polypeptide, a nucleic acid encoding an uridine 5'-diphosphoglucosyl transferase (UGT) polypeptide and/or a nucleic acid encoding a vanillyl alcohol oxidase (VAO). Microorganism such as *Saccharomyces cerevisiae, Schizosaccharomyces pombe* or *Escherichia coli* are provided as are plant or plant cells such as *Physcomitrella* or tobacco.

A recombinant yeast cell; a vanillin and/or vanillin glucoside extract isolated from the recombinant host cell or recombinant yeast cell; a consumable, e.g., a food product, pharmaceutical composition, a dietary supplement, a nutraceutical, a dental hygienic composition, a tabletop sweetener, or a cosmetic product containing the extract; and a method for producing vanillin and/or vanillin beta-D-glucoside are also provided.

DETAILED DESCRIPTION OF THE INVENTION

Figure 1:
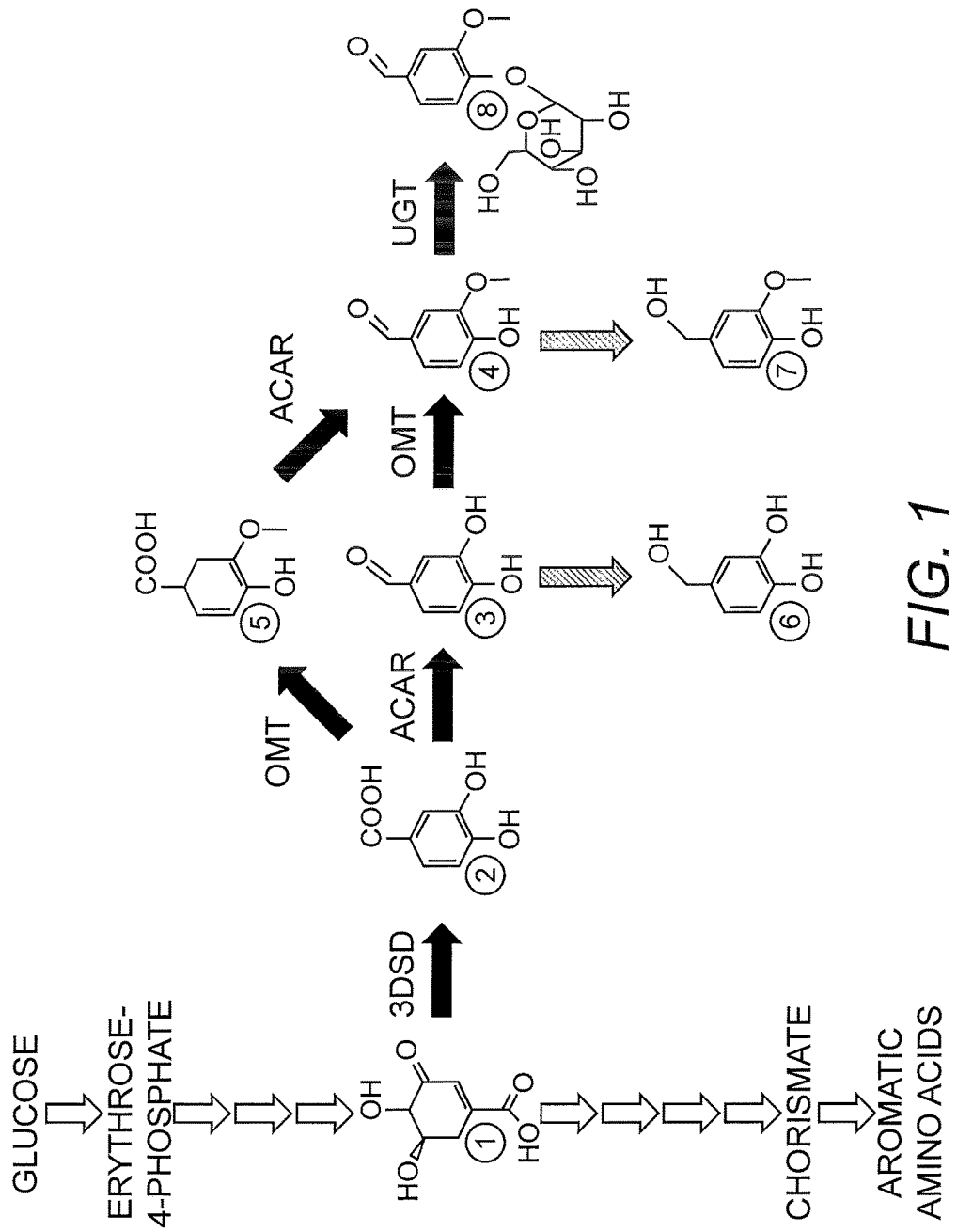
FIG. 1 is a schematic of de novo biosynthesis of vanillin (4) and outline of the different vanillin catabolites and metabolic side products, i.e., dehydroshikimic acid (1), protocatechuic acid (2), protocatechuic aldehyde (3), vanillic acid (5), protocatechuic alcohol (6), vanillyl alcohol (7), and vanillin β-D-glucoside (8), found in an organism expressing 3DSD, ACAR, OMT, and UGT and a phophopantheteine transferase (PPTase). Open arrows show primary metabolic reactions in yeast; black arrows show enzyme reactions introduced by metabolic engineering; diagonally striped arrows show undesired inherent yeast metabolic reactions.

This invention is based on the discovery that knocking out certain alcohol dehydrogenases and/or aldehyde reductases, or similar enzymes, lowers the amount of vanillic alcohol that is formed as a byproduct. See FIGS. 1 and 2. This is of commercial importance because the presence of alcohol creates inefficiencies in certain steps of the downstream purification of vanillin or vanillin glucoside if the alcohol is allowed to accumulate.

Therefore, the present invention is a recombinant host that is capable of producing vanillin or vanillin glucoside, but fails to produce, or has reduced production of, one or more alcohol dehydrogenases and/or one or more aldehyde reductases. A recombinant host that produces or is capable of producing vanillin or vanillin glucoside is a host cell that expresses the necessary biosynthetic enzymes to produce vanillin or vanillin glucoside from a primary substrate, e.g., glucose, or from an intermediate molecule, e.g., dehydroshikimic acid, protocatechuic acid, protocatechuic aldehyde, or vanillic acid. See FIG. 1.

A recombinant host that fails to produce an enzyme, has reduced production of an enzyme, or lacks a functional enzyme, includes an organism that have been recombinantly modified such that the gene encoding the enzyme is knocked out, an organism with one or more point mutations in the enzyme which reduces or diminishes enzyme activity, or an organism wherein the promoter of the gene encoding the enzyme has been modified or removed so that the enzyme is not expressed or expressed at a reduced level compared to a wild-type organism.

Many methods for genetic modification of target genes are known to one skilled in the art and may be used to create the recombinant host of this invention. Modifications that may be used to reduce or eliminate expression of a target enzyme are disruptions that include, but are not limited to, deletion of the entire gene or a portion of the gene encoding an enzyme; inserting a DNA fragment into a gene encoding the enzyme (in either the promoter or coding region) so that the enzyme is not expressed or expressed at lower levels; introducing a mutation into the coding region for the enzyme, which adds a stop codon or frame shift such that a functional enzyme is not expressed; and introducing one or more mutations into the coding region of an enzyme to alter amino acids so that a non-functional or a less enzymatically active enzyme is expressed. In addition, expression of an enzyme may be blocked by expression of an antisense RNA or an interfering RNA, and constructs may be introduced that result in cosuppression. In addition, the synthesis or stability of the transcript may be lessened by mutation. Similarly, the efficiency by which an enzyme is translated from mRNA may be modulated by mutation. All of these methods may be readily practiced by one skilled in the art making use of the known sequences encoding the alcohol dehydrogenases and/or aldehyde reductases of this invention.

Alcohol dehydrogenase and aldehyde reductase sequences from a variety of organisms are well-known in the art and the selection of the target gene(s) will be dependent upon the host selected. Representative alcohol dehydrogenase (ADH) and aldehyde reductase sequences, which may be targeted in accordance with the present invention are listed in Table 1. One skilled in the art may choose specific modification strategies to eliminate or lower the expression of an alcohol dehydrogenase and/or aldehyde reductase as desired to facilitate vanillin and/or vanillin glucoside production.

dinated by NCBI (National Center for Biotechnology Information) with identifying BioProject Nos. PRJNA128, PRJNA13838, PRJNA43747, PRJNA48559, PRJNA52955, PRJNA48569, PRJNA39317. Additional examples of yeast genomic sequences include that of *Schizosaccharomyces pombe*, which is included in BioProject Nos. PRJNA127, PRJNA13836, and PRJNA20755. Genomic sequences of plants are also known in the art and the genomic sequence of *Arabidopsis thaliana* is included in BioProject Nos. PRJNA116, PRJNA10719, PRJNA13190, and PRJNA30811. Other genomic sequences can be readily found by one of skill in the art in publicly available databases.

In particular, DNA sequences surrounding an alcohol dehydrogenase or aldehyde reductase coding sequence are useful for modification methods using homologous recombination. For example, sequences flanking the gene of interest are placed on either side of a selectable marker gene to mediate homologous recombination whereby the marker gene replaces the gene of interest. Also partial gene sequences and flanking sequences bounding a selectable marker gene may be used to mediate homologous recombination whereby the marker gene replaces a portion of the target gene. In addition, the selectable marker may be bounded by site-specific recombination sites, so that following expression of the corresponding site-specific recombinase, the resistance gene is excised from the gene of interest without reactivating the latter. The site-specific recombination leaves behind a recombination site which disrupts expression of the alcohol dehydrogenase or aldehyde reduc-

TABLE 1

| Source | Target | Amino Acid Sequence Accession No. | SEQ ID NO: | Nucleotide Sequence Accession No. | SEQ ID NO: |
| --- | --- | --- | --- | --- | --- |
| S. cerevisiae | Adh6 | NP_014051 | 1 | NM_001182831 | 2 |
| S. cerevisiae | Adh7 | NP_010030 | 3 | NM_001178812 | 4 |
| S. cerevisiae | GRE2 | NP_014490 | 5 | NM_001183405 | 6 |
| S. cerevisiae | YDR541C | NP_010830 | 7 | NM_001180849 | 8 |
| S. cerevisiae | ARI1 | NP_011358 | 9 | NM_001181022 | 10 |
| S. cerevisiae | YGL039W | NP_011476 | 11 | NM_001180904 | 12 |
| S. pombe | SPAC513.07 | NP_593981 | 13 | NM_001019407 | 14 |
| Arabidopsis thaliana | CAD3 | NP_179780 | 15 | NM_127758 | 16 |
| A. thaliana | CAD9 | NP_195643 | 17 | NM_120093 | 18 |
| A. thaliana | CAD2 | NP_179765 | 19 | NM_127743 | 20 |
| A. thaliana | AT1G51410 | NP_175552 | 21 | NM_104019 | 22 |
| A. thaliana | AT5G19440 | NP_197445 | 23 | NM_121949 | 24 |

In some embodiments, the recombinant host cells has reduced production or activity of a first alcohol dehydrogenase and reduced production of one or more second alcohol dehydrogenases, one or more aldehyde reductases, or a combination thereof. In particular embodiments, the first alcohol dehydrogenase is ADH6 or an ortholog thereof, e.g., CAD9, CAD3 or CAD2 from *A. thaliana*. In another embodiment, the one or more second alcohol dehydrogenases are selected from the group of ADH7, GRE2 (Genes de Respuesta a Estres 2), or an ortholog thereof, e.g., AT1G51410 or AT5G19440; and the aldehyde reductase is selected from the group of ARI1 (Aldehyde Reductase Intermediate 1), Aldehyde Reductase YGL039W, or an ortholog thereof, e.g., SPAC513.07 or YDR541C).

DNA sequences surrounding one or more of the above-referenced sequence are also useful in some modification procedures and are available for yeasts such as for *Saccharomyces cerevisiae* in the complete genome sequence coortase. The homologous recombination vector may be constructed to also leave a deletion in the gene of interest following excision of the selectable marker, as is well known to one skilled in the art.

Deletions may be made using mitotic recombination as described in Wach, et al. ((1994) *Yeast* 10:1793-1808). This method involves preparing a DNA fragment that contains a selectable marker between genomic regions that may be as short as 20 bp, and which bound a target DNA sequence. This DNA fragment can be prepared by PCR amplification of the selectable marker gene using as primers oligonucleotides that hybridize to the ends of the marker gene and that include the genomic regions that can recombine with the yeast genome. The linear DNA fragment can be efficiently transformed into yeast and recombined into the genome resulting in gene replacement including with deletion of the target DNA sequence.

Moreover, promoter replacement methods may be used to exchange the endogenous transcriptional control elements allowing another means to modulate expression such as described in Mnaimneh, et al. ((2004) *Cell* 118(1):31-44).

Hosts cells of use in this invention include any organism capable of producing vanillin and/or vanillin glucoside either naturally or synthetically, e.g., by recombinant expression of one or more genes of the vanillin and/or vanillin glucoside biosynthetic pathway (FIG. 1). A number of prokaryotes and eukaryotes are suitable for use in constructing the recombinant microorganisms described herein, e.g., gram-negative bacteria, gram-positive bacteria, yeast or other fungi. A species and strain selected for use as a vanillin and/or vanillin glucoside production strain is first analyzed to determine which production genes are endogenous to the strain and which genes are not present. Genes for which an endogenous counterpart is not present in the strain are assembled in one or more recombinant constructs, which are then transformed into the strain in order to supply the missing function(s).

Exemplary prokaryotic and eukaryotic species are described in more detail below. However, it will be appreciated that other species may be suitable. For example, suitable species may be in a genus *Agaricus, Aspergillus, Bacillus, Candida, Corynebacterium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces Yarrowia* and *Lactobacillus*. Exemplary species from such genera include *Lentinus tigrinus, Laetiporus sulphureus, Phanerochaete chrysosporium, Pichia pastoris, Physcomitrella patens, Rhodoturula glutinis* 32, *Rhodoturula mucilaginosa, Phaffia rhodozyma* UBV-AX, *Xanthophyllomyces dendrorhous, Fusarium fujikuroi/Gibberella fujikuroi, Candida utilis* and *Yarrowia lipolytica*. In some embodiments, a microorganism can be an Ascomycete such as *Gibberella fujikuroi, Kluyveromyces lactis, Schizosaccharomyces pombe, Aspergillus niger*, or *Saccharomyces cerevisiae*. In some embodiments, a microorganism can be a prokaryote such as *Escherichia coli, Rhodobacter sphaeroides*, or *Rhodobacter capsulatus*. It will be appreciated that certain microorganisms can be used to screen and test genes of interest in a high throughput manner, while other microorganisms with desired productivity or growth characteristics can be used for large-scale production of vanillin beta-D-glucoside.

Specific non-limiting examples of useful recombinant hosts are described in WO 01/40491, as well as in Hansen et al. (2009) *Appl. Environ. Microbiol.* 75:2765-2774 and Brochado, et al. (2010) *Microbial Cell Factories* 9:84, wherein the recombinant host according to this invention contains a heterologous nucleic acid encoding a mutant COMT polypeptide and/or mutant AROM polypeptide instead of the OMT genes described in WO 01/40491.

One preferred recombinant host to use with the present invention is *S. cerevisiae*, which may be recombinantly engineered as described herein. *S. cerevisiae* is a widely used chassis organism in synthetic biology, and can be used as the recombinant microorganism platform. There are libraries of mutants, plasmids, detailed computer models of metabolism and other information available for *S. cerevisiae*, allowing for rational design of various modules to enhance product yield. Methods are known for making recombinant microorganisms. The VG4 strain of *S. cerevisiae* (Brochado, et al. (2010) *Microb. Cell Fact.* 9:84) is particularly useful. VG4 has the genotype of pdc1Δgdh1Δ↑GDH2.

*Aspergillus* species such as *A. oryzae, A. niger* and *A. sojae* are widely used microorganisms in food production, and can also be used as the recombinant microorganism platform. Thus, the recombinant host may be *Aspergillus* spp. Nucleotide sequences are available for genomes of *A. nidulans, A. fumigatus, A. oryzae, A. clavatus, A. flavus, A. niger*, and *A. terreus*, allowing rational design and modification of endogenous pathways to enhance flux and increase product yield. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for the production of food ingredients such as vanillin and vanillin glucoside.

*E. coli*, another widely used platform organism in synthetic biology, can also be used as the recombinant microorganism platform. Thus, the recombinant host may be *E. coli*. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Rhodobacter* can be used as the recombinant microorganism platform. Thus, the recombinant host may be *Rhodobacter* spp. Similar to *E. coli*, there are libraries of mutants available as well as suitable plasmid vectors, allowing for rational design of various modules to enhance product yield. Methods similar to those described above for *E. coli* can be used to make recombinant *Rhodobacter* microorganisms.

*Physcomitrella* mosses, when grown in suspension culture, have characteristics similar to yeast or other fungal cultures. This genera is becoming an important type of cell for production of plant secondary metabolites, which can be difficult to produce in other types of cells. Thus, the recombinant host may be a *Physcomitrella* spp.

In some embodiments, the recombinant host is a plant or plant cells that includes the one or more genes of the vanillin and/or vanillin glucoside biosynthetic pathway. A plant or plant cell can be modified to express the vanillin and/or vanillin glucoside biosynthetic pathway with a concurrent knockout of one or more alcohol dehydrogenases and/or aldehyde reductases. The plant or plant cells can be stably transformed to retain the introduced nucleic acid with each cell division. A plant or plant cell can also be transiently transformed such that the heterologous nucleic acid is not integrated into its genome. Transiently transformed cells typically lose all or some portion of the introduced nucleic acid with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a heterologous nucleic acid, for example a recombinant nucleic acid construct into other lines, to transfer a heterologous nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation; see U.S. Pat. Nos. 5,538,880; 5,204,253; 6,329,571; and 6,013,863. If a cell or cultured tissue is used as the recipient tissue for transformation, plants can be regenerated from transformed cultures if desired, by techniques known to those skilled in the art.

A population of transgenic plants can be screened and/or selected for those members of the population that have a trait or phenotype conferred by expression of the transgene. For example, a population of progeny of a single transformation event can be screened for those plants having a desired level of expression of a polypeptide or nucleic acid described herein. Physical and biochemical methods can be used to identify expression levels. These include Southern analysis or PCR amplification for detection of a polynucleotide; northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, western blots, immunoprecipitation, and enzyme-linked immunoassays to detect polypeptides. Other techniques such as in situ hybridization, enzyme staining, and immunostaining also can be used to detect the presence or expression of polypeptides and/or nucleic acids. Methods for performing all of the referenced techniques are known.

As an alternative, a population of plants with independent transformation events can be screened for those plants having a desired trait, such as production of vanillin glucoside and lack of vanillic alcohol production. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant.

Depending on the particular organism used in this invention, the recombinant host cell can naturally or recombinantly express genes encoding an AROM (A=Multifunctional Enzyme), OMT (O-methyltransferase), COMT (Catechol-O-Methyl Transferase), 3DSD (3-dehydroshikimate dehydratase), ACAR (aromatic carboxylic acid reductase), UGT (uridine 5'-diphosphoglucosyl transferase), or PPTase (phosphopantetheine transferase) (FIG. 1).

Recombinant expression means that the genome of a host cell has been augmented through the introduction of one or more recombinant genes, which include regulatory sequences that facilitate the transcription and translation of a protein of interest. While embodiments include stable introduction of recombinant genes into the host genome, autonomous or replicative plasmids or vectors can also be used within the scope of this invention. Moreover, the present invention can be practiced using a low copy number, e.g., a single copy, or high copy number (as exemplified herein) plasmid or vector.

Generally, the introduced recombinant gene is not originally resident in the host that is the recipient of the recombinant gene, but it is within the scope of the invention to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms, plant cells, and plants.

The term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene may be a DNA sequence from another species, or may be a DNA sequence that originated from or is present in the same species, but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA.

A recombinant gene encoding a polypeptide described herein includes the coding sequence for that polypeptide, operably linked, in sense orientation, to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. The term "heterologous nucleic acid" as used herein, refers to a nucleic acid introduced into a recombinant host, wherein said nucleic acid is not naturally present in said host. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically includes at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

One or more genes, for example one or more heterologous nucleic acids, can be combined in a recombinant nucleic acid construct in "modules" useful for a discrete aspect of vanillin and/or vanillin glucoside production. Combining a plurality of genes or heterologous nucleic acids in a module, facilitates the use of the module in a variety of species. For example, a vanillin gene cluster can be combined such that each coding sequence is operably linked to a separate regulatory region, to form a vanillin module for production in eukaryotic organisms. Alternatively, the module can express a polycistronic message for production of vanillin and/or vanillin glucoside in prokaryotic hosts such as species of Rodobacter, E. coli, Bacillus or Lactobacillus. In addition to genes useful for vanillin or vanillin glucoside production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

As indicated, recombinant hosts can express one or more enzymes involved in the biosynthesis of the vanillin or vanillin glucoside, as well as additional genes or biosynthetic modules that improve efficiency with which energy and carbon sources are converted to vanillin and its glucoside, and/or to enhance productivity from the cell culture or plant. In certain embodiments, the recombinant host endogenously ore recombinantly expresses genes encoding AROM, COMT, 3DSD, ACAR, UGT, and/or PPTase.

AROM is a penta-functional enzyme complex encoded in yeast by the ARO1 gene. The gene is 4764 bp long and encodes a corresponding polypeptide 1588 amino acids in length. AROM performs five consecutive enzymatic conversions, i.e., converting DAHP (3-deoxy-D-arabino-heptulosonic acid-7-phosphate) into 3-DHQ (3-dehydroquinate), which is converted to 3-DHS (3-dehydroshikimic acid), which is converted to shikimate, which is converted to shikimate-3-P (shikimate 3-phosphate), which is converted into EPSP (5-enolpyruvylskimate 3-phosphate), all en route to cellular biosynthesis of the aromatic amino acids tyrosine, tryptophan and phenylalanine. According to some embodiments of this invention, the AROM enzyme possesses at least four of the five enzymatic activities of the *S. cerevisiae* AROM polypeptide, i.e., 3-dehydroquinate dehydratase activity, 3-dehydroquinate synthase activity, 3-phosphoshikimate 1-carboxyvinyltransferase activity, shikimate 3-dehydrogenase (NADP+) activity, and shikimate kinase activity.

Non-limiting examples of AROM polypeptides include the *Saccharomyces cerevisiae* polypeptide available under GENBANK Accession No. X06077; the *Schizosaccharomyces pombe* polypeptide available under GENBANK Accession No. NP_594681.1; *Schizosaccharomyces japonicas* polypeptide available under GENBANK Accession No. XP_002171624; *Neurospora crassa* polypeptide available under GENBANK Accession No. XP_956000; and the *Yarrowia lipolytica* polypeptide available under GENBANK Accession No. XP_505337.

According to one embodiment of this invention, the AROM polypeptide is a mutant AROM polypeptide with decreased shikimate dehydrogenase activity. When expressed in a recombinant host, the mutant AROM polypeptide redirects metabolic flux from aromatic amino acid production to vanillin precursor production, i.e., 3-DHS. See WO 2013/022881. In certain embodiments, the mutant AROM polypeptide described herein can have one or more modifications in domain 5 (e.g., a substitution of one or more amino acids, a deletion of one or more amino acids, insertions of one or more amino acids, or combinations of substitutions, deletions, and insertions).

In some embodiments, a modified AROM polypeptide is fused to a polypeptide catalyzing the first committed step of vanillin biosynthesis, 3DSD. A polypeptide having 3DSD activity and that is suitable for use in a fusion polypeptide includes the 3DSD polypeptide from *Podospora pauciseta, Ustilago maydis, Rhodoicoccus jostii, Acinetobacter* sp., *Aspergillus niger* or *Neurospora crassa*. See, GENBANK Accession Nos. CAD60599), XP_001905369.1, XP_761560.1, ABG93191.1, AAC37159.1, and XM_001392464.

Alternatively, or in addition to, the recombinant host can express a COMT polypeptide. Non-limiting examples of COMT polypeptides of use in this invention include COMT polypeptides in the family classified under EC number 2.1.1.6, such as the *Homo sapiens* (Hs) polypeptide available under GENBANK Accession No. NM_000754; an *Arabidopsis thaliana* polypeptide available under GENBANK Accession No. AY062837; or a *Fragariaxananassa* (strawberry) polypeptide available under GENBANK Accession No. AF220491. Human COMT polypeptide exists as several variants and the COMT polypeptide may be any of these variants. Other suitable mammalian COMT polypeptides of use in this invention include, but are not limited to, those isolated from Pan troglodytes (GENBANK Accession No. XP_514984), *Macaca mulatta* (GENBANK Accession No. AFJ70145), *Equus caballus* (GENBANK Accession No. NP_001075303), *Canis lupus familiaris* (GENBANK Accession No. AAR20324), *Cricetulus griseus* (GENBANK Accession No. EGV97595), *Sus scrofa* (GENBANK Accession No. NP_001182259), and *Bos taurus* (GENBANK Accession No. NP_001095787). Other exemplary COMT polypeptides from plant and microorganism sources include, but are not limited to, those isolated from *Rosa chinensis* (GENBANK Accession No. CAD29457), *Prunus dulcis* (GENBANK Accession No. CAA58218), *Gossypium hirsutum* (GENBANK Accession No. ACT32028), *Jatropha curcas* (GENBANK Accession No. ACT87981), *Eucalyptus camaldulensis* (ADB82906), *Candida orthopsilosis* (GENBANK Accession No. CCG25047), *Pichia stipitis* (GENBANK Accession No. ABN67921), and *Spathaspora passalidarum* (GENBANK Accession No. EGW29958). In certain embodiments, the COMT polypeptide of the invention is obtained from *Phytophthera infestans* (GENBANK Accession No. XP_002899214), *Catharanthus roseus* (GENBANK Accession No. EGS21863), *Yarrowia lipolytica* (GENBANK Accession No. XP 500451), *Ciona intestinalis* (GENBANK Accession No. XP_002121420 or XP_002131313), *Capsasproa owczarzaki* (GENBANK Accession No. EFW46044), *Chaetomium therophilum* (GENBANK Accession No. EGS21863), *Clavispora lusitaniae* (GENBANK Accession No. XP_002899214), *Paracoccidioides* sp. 'lutzii' Pb01 (GENBANK Accession No. XP_002793380), *Vanilla planifolia* (see SEQ ID NO:56 of PCT/US2012/049842), *Coffea Arabica* (GENBANK Accession No. AAN03726), *Rattus norvegicus* (GENBANK Accession No. NP_036663), *Mus musculus* (GENBANK Accession No. NP_031770), *Crenarchaeote* (GENBANK Accession No. ABZ07345), *Mycobacterium vanbaleeni* (GENBANK Accession No. ABM14078), or *Schizosaccharomyces pombe* (GENBANK Accession No. NP_001018770.

In some embodiments, a mutant COMT polypeptide is used to improve biosynthesis of vanillin beta-D-glucoside. For example, mutant COMT polypeptides can have one or more of the following properties: increased turnover; preferential methylation at the meta (3') position, rather than at the para (4') position such that production of vanillin is favored over isovanillin; or better specificity for the vanillin pathway substrates, protocatechuic acid and protocatechuic aldehyde. See WO 2013/022881. A mutant COMT polypeptide can have one or more mutations (e.g., a substitution of one or more amino acids, a deletion of one or more amino acids, insertions of one or more amino acids, or combinations of substitutions, deletions, and insertions) in, for example, the substrate binding site. For example, a mutant COMT polypeptide can have one or more amino acid substitutions in the substrate binding site of human COMT.

In one embodiment, a mutant COMT polypeptide is provided, which is capable of catalyzing methylation of an —OH group of protocatechuic acid, wherein said methylation results in generation of at least 4 times more vanillic acid compared to iso-vanillic acid. In another embodiment, the mutant COMT polypeptide is capable of catalyzing methylation of an —OH group of protocatechuic aldehyde, wherein said methylation results in generation of at least 4 times more vanillin compared to iso-vanillin.

In some embodiments, the host harbors a nucleic acid encoding mutant AROM polypeptide and optionally a wild-type COMT polypeptide. In another embodiment, the host of this invention harbors a nucleic acid encoding mutant COMT polypeptide and optionally a wild-type AROM polypeptide. In yet another embodiment, the host of this invention harbors a nucleic acid encoding mutant AROM polypeptide and optionally a mutant COMT polypeptide.

Suitable 3DSD polypeptides are known. A 3DSD polypeptide according to the present invention may be any enzyme with 3-dehydroshikimate dehydratase activity. Preferably, the 3DSD polypeptide is an enzyme capable of catalyzing conversion of 3-dehydro-shikimate to protocatechuate and $H_2O$. A 3DSD polypeptide according to the present invention is preferably an enzyme classified under EC 4.2.1.118. For example, a suitable polypeptide having 3DSD activity includes the 3DSD polypeptide made by *Podospora pauciseta, Ustilago maydis, Rhodoicoccus jostii, Acinetobacter* sp., *Aspergillus niger* or *Neurospora crassa*. See, GENBANK Accession Nos. CAD60599, XP_001905369.1, XP_761560.1, ABG93191.1, AAC37159.1, and XM_001392464. Thus, the recombinant host may include a heterologous nucleic acid encoding the 3DSD polypeptide of *Podospora anserina, Ustilago maydis, Rhodoicoccus jostii, Acinetobacter* sp., *Aspergillus niger* or *Neurospora crassa* or a functional homologue of any of the aforementioned sharing at least 80%, such as at least 85%, for example at least 90%, such as at least 95%, for example at least 98% sequence identity therewith.

Suitable ACAR polypeptides are also known in the art. An ACAR polypeptide according to the present invention may be any enzyme having aromatic carboxylic acid reductase activity. Preferably, the ACAR polypeptide is an enzyme capable of catalyzing conversion protocatechuic acid to protocatechuic aldehyde and/or conversion of vanillic acid to vanillin. An ACAR polypeptide according to the present invention is preferably an enzyme classified under EC 1.2.1.30. For example a suitable ACAR polypeptide is made by *Nocardia* sp. See, e.g., GENBANK Accession No. AY495697. Thus, the recombinant host may include a heterologous nucleic acid encoding the ACAR polypeptide of *Nocardia* sp. or a functional homologue thereof sharing at least 80%, such as at least 85%, for example at least 90%, such as at least 95%, for example at least 98% sequence identity therewith.

Suitable PPTase polypeptides are known. A PPTase polypeptide according to the present invention may be any enzyme capable of catalyzing phosphopantetheinylation. Preferably, the PPTase polypeptide is an enzyme capable of catalyzing phosphopantetheinylation of ACAR. For example, a suitable PPTase polypeptide is made by *E. coli*,

*Corynebacterium glutamicum*, or *Nocardia farcinica*. See GENBANK Accession Nos. NP_601186, BAA35224, and YP_120266. Thus, the recombinant host may include a heterologous nucleic acid encoding the PPTase polypeptide of *E. coli*, *C. glutamicum*, or *N. farcinica* or a functional homologue of any of the aforementioned sharing at least 80%, such as at least 85%, for example at least 90%, such as at least 95%, for example at least 98% sequence identity therewith.

Glucosylation of vanillin is particularly useful. Vanillin-β-D-glucoside is the storage form of vanillin found in the vanilla pod. It is non-toxic to most organisms, including yeast, and has a higher solubility in water, as compared to vanillin. In addition, the formation of vanillin-β-D-glucoside most likely directs the biosynthesis toward vanillin production. UGT72E2 (Hansen, et al. (2009) *Appl. Environ. Microbiol.* 75:2765-27740) exhibited high substrate specificity toward vanillin. In concordance with this observation, its expression in the vanillin producing *S. cerevisiae* strain resulted in almost all vanillin being converted into vanillin-β-D-glucoside. The ability to turn vanillin into vanillin-3-D-glucoside in vivo is important, because microbial production of non-glucosylated vanillin beyond the 0.5-1 g/liter scale would be hampered by the toxicity of free vanillin. Glucosylation serves to circumvent the inhibitory effect.

Accordingly, the recombinant host of this invention can also express a UGT polypeptide. A UGT polypeptide may be any UDP-Glucose:Aglycon-Glucosyltransferase. Preferably the UGT polypeptides can catalyze the glucosylation of vanillin (i.e., to produce vanillin beta-D-glucoside). Thus, the UGT polypeptide may be a Family 1 glycosyltransferease. Preferred UGT polypeptides according to the invention are classified under EC 2.4.1. Suitable UGT polypeptides include the UGT71C2, UGT72B1, UGT72E2, UGT84A2, UGT89B1, UGT85B1, and arbutin synthase polypeptides. See, e.g., GENBANK Accession Nos. AC0005496, NM_116337, and NM_126067. The *A. thaliana* UGT72E2 is particularly useful (see, e.g., Hansen, et al. (2009) supra). Thus, the recombinant host may include a heterologous nucleic acid encoding the UGT71C2, UGT72B1, UGT72E2, UGT84A2, UGT89B1, UGT85B1, or arbutin synthase or a functional homologue of any of the aforementioned sharing at least 80%, such as at least 85%, for example at least 90%, such as at least 95%, for example at least 98% sequence identity therewith. Other useful UGTs are described in WO 01/40491.

As a further embodiment of this invention, a VAO enzyme (EC 1.1.3.38) can also be expressed by host cells to oxidize any residual vanillyl alcohol into vanillin. VAO enzymes are known in the art and include, but are not limited to enzymes from filamentous fungi such as *Fusarium monilifomis* (GENBANK Accession No. AFJ11909) and *Penicillium simplicissium* (GENBANK Accession No. P56216; Benen, et al. (1998) *J. Biol. Chem.* 273:7865-72) and bacteria such as *Modestobacter marinus* (GENBANK Accession No. YP_006366868), *Rhodococcus jostii* (GENBANK Accession No. YP_703243.1) and *R. opacus* (GENBANK Accession No. EHI39392).

In some cases, it is desirable to inhibit one or more functions of an endogenous polypeptide in order to divert metabolic intermediates toward vanillin or vanillin glucoside biosynthesis. For example, pyruvate decarboxylase (PDC1) and/or glutamate dehydrogenase activity can be reduced. In such cases, a nucleic acid that inhibits expression of the polypeptide or gene product may be included in a recombinant construct that is transformed into the strain. Alternatively, mutagenesis can be used to generate mutants in genes for which it is desired to inhibit function.

To demonstrate expression and activity of one or more of the above-referenced enzymes expressed by the recombinant host, levels of products, substrates and intermediates, e.g., dehydroshikimic acid, protocatechuic acid, protocatechuic aldehyde, vanillin, and vanillin beta-D-glucoside produced by the recombinant host can be determined by extracting samples from culture media for analysis according to published methods.

Recombinant hosts described herein can be used in methods to produce vanillin or vanillin glucoside. For example, if the recombinant host is a microorganism, the method can include growing the recombinant microorganism in a culture medium under conditions in which vanillin and/or vanillin glucoside biosynthesis genes are expressed. The recombinant microorganism may be grown in a batch, fed batch or continuous process or combinations thereof. Typically, the recombinant microorganism is grown in a fermentor at a defined temperature(s) in the presence of a suitable nutrient source, e.g., a carbon source, for a desired period of time to produce a desired amount of vanillin and/or vanillin glucoside.

Therefore, this invention also provides a method for producing vanillin and/or vanillin beta-D-glucoside by providing a recombinant host that produces vanillin and/or vanillin beta-D-glucoside and has reduced production or activity of at least one (or two, three, four, five, six, seven, eight, nine or ten) alcohol dehydrogenase, at least one aldehyde reductase, or at least one alcohol dehydrogenase and at least one aldehyde reductase; cultivating said recombinant host, e.g., in the presence of a suitable carbon source, for a time sufficient for said recombinant host to produce vanillin and/or vanillin glucoside; and isolating vanillin and/or vanillin glucoside from said recombinant host or from the cultivation supernatant. In one embodiment, the recombinant host produces a reduced amount of vanillic alcohol in comparison to a host that expresses the one or more functional alcohol dehydrogenases or one or more aldehyde reductases.

In certain embodiments, it is preferred that the recombinant host expresses at least one 3DSD and at least one ACAR, which preferably may be one of the 3DSD's and ACAR's described herein. In embodiments where the recombinant host expresses an ACAR capable of catalyzing conversion of vanillic acid to vanillin, then the method may also include determining the level of generated vanillin and iso-vanillin. The recombinant host may also express at least one UGT capable of catalyzing glucosylation of vanillin and isovanillin, in which case the levels of vanillin-glucoside and iso-vanillin-glucoside may be determined instead of the levels of vanillin and iso-vanillin, respectively. Alternatively, this may be determined by generating a recombinant host harboring a heterologous nucleic acid encoding the mutant COMT polypeptide to be tested, and feeding protocatechuic acid to said recombinant host, followed by determining the level of generated iso-vanillic acid and vanillic acid.

Similarly, an in vitro assay or a recombinant host cell can be used to determine whether a mutant COMT polypeptide is capable of catalyzing methylation of an —OH group of protocatechuic aldehyde, wherein said methylation results in generation of at least X times more vanillin compared to iso-vanillin. However, in this assay, protecatechuic aldehyde is used as starting material and the level of vanillin and iso-vanillin is determined.

Likewise, an in vitro assay or a recombinant host cell can be used to determine whether a given mutant COMT polypeptide is capable of catalyzing methylation of an —OH group of protocatechuic alcohol, wherein said methylation results in generation of at least X times more vanillyl alcohol compared to iso-vanillyl alcohol. However, in this assay, protecatechuic alcohol is used as starting material and the level of vanillyl alcohol and iso-vanillyl alcohol is determined.

The level of isovanillin and vanillin may be determined by any suitable method useful for detecting these compounds, wherein said method can distinguish between iso-vanillin and vanillin. Such methods include for example HPLC. Similarly, the level of iso-vanillic acid, vanillic acid, iso-vanillyl alcohol and vanillyl alcohol may be determined using any suitable method useful for detecting these compounds, wherein said method can distinguish between iso-vanillin and vanillin. Such methods include for example HPLC.

Carbon sources of use in the method of this invention include any molecule that can be metabolized by the recombinant host cell to facilitate growth and/or production of the vanillin and/or vanillin glucoside. Examples of suitable carbon sources include, but are not limited to, sucrose (e.g., as found in molasses), fructose, xylose, ethanol, glycerol, glucose, cellulose, starch, cellobiose or other glucose containing polymer. In embodiments employing yeast as a host, for example, carbons sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

After the recombinant host has been grown in culture for the desired period of time, vanillin and/or vanillin beta-D-glucoside can then be recovered from the culture using various techniques known in the art, e.g., isolation and purification by extraction, vacuum distillation and multistage re-crystallization from aqueous solutions and ultrafiltration (Böddeker, et al. (1997) *J. Membrane Sci.* 137:155-158; Borges da Silva, et al. (2009) *Chem. Eng. Des.* 87:1276-1292). Two-phase extraction processes, employing either sulphydryl compounds, such as dithiothreitol, dithioerythritol, glutathione, or L-cysteine (U.S. Pat. No. 5,128,253), or alkaline KOH solutions (WO 94/13614), have been used in the recovery of vanillin as well as for its separation from other aromatic substances. Vanillin adsorption and pervaporation from bioconverted media using polyetherpolyamide copolymer membranes has also been described (Böddeker, et al. (1997) supra; Zucchi, et al. (1998) *J. Microbiol. Biotechnol.* 8:719-722). Macroporous adsorption resins with crosslinked-polystyrene framework have also been used to recover dissolved vanillin from aqueous solutions (Zhang, et al. (2008) *Eur. Food Res. Technol.* 226:377-383). Ultrafiltration and membrane contactor (MC) techniques have also been evaluated to recover vanillin (Zabkova, et al. (2007) *J. Membr. Sci.* 301:221-237; Scuibba, et al. (2009) *Desalination* 241:357-364). Alternatively, conventional techniques such as percolation or supercritical carbon dioxide extraction and reverse osmosis for concentration could be used. If the recombinant host is a plant or plant cells, vanillin or vanillin glucoside can be extracted from the plant tissue using various techniques known in the art.

In some embodiments, vanillin or vanillin beta-D-glucoside can be produced using whole cells that are fed raw materials that contain precursor molecules. The raw materials may be fed during cell growth or after cell growth. The whole cells may be in suspension or immobilized. The whole cells may be in fermentation broth or in a reaction buffer. In some embodiments a permeabilizing agent may be required for efficient transfer of substrate into the cells.

In some embodiments, the vanillin or vanillin beta-D-glucoside is isolated and purified to homogeneity (e.g., at least 90%, 92%, 94%, 96%, or 98% pure). In other embodiments, the vanillin or vanillin beta-D-glucoside is isolated as an extract from a recombinant host. In this respect, vanillin or vanillin beta-D-glucoside may be isolated, but not necessarily purified to homogeneity. Desirably, the amount of vanillin or vanillin beta-D-glucoside produced can be from about 1 mg/l to about 20,000 mg/L or higher. For example about 1 to about 100 mg/L, about 30 to about 100 mg/L, about 50 to about 200 mg/L, about 100 to about 500 mg/L, about 100 to about 1,000 mg/L, about 250 to about 5,000 mg/L, about 1,000 to about 15,000 mg/L, or about 2,000 to about 10,000 mg/L of vanillin or vanillin beta-D-glucoside can be produced. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of recombinant microorganisms is used, they can be grown in a mixed culture to produce vanillin and/or vanillin glucoside.

Extracts of isolated, and optionally purified, vanillin or vanillin beta-D-glucoside find use in flavoring consumables such as food products, dietary supplements, nutraceuticals, pharmaceutical compositions, dental hygienic compositions, and cosmetic products.

The phrase "food product," as used herein, includes, but is not limited to, fruits, vegetables, juices, meat products such as ham, bacon and sausage; egg products, fruit concentrates, gelatins and gelatin-like products such as jams, jellies, preserves, and the like; milk products such as ice cream, sour cream and sherbet; icings, syrups including molasses; corn, wheat, rye, soybean, oat, rice and barley products, nut meats and nut products, cakes, cookies, confectionaries such as candies, gums, fruit flavored drops, and chocolates, chewing gum, mints, creams, icing, ice cream, pies and breads, beverages such as coffee, tea, carbonated soft drinks, such as COKE and PEPSI, non-carbonated soft drinks, juices and other fruit drinks, sports drinks such as GATORADE, coffee, teas, iced teas, cola, alcoholic beverages, such as beers, wines and liquors, and KOOL-AID.

Food products also include condiments such as herbs, spices and seasonings, flavor enhancers. A food product also includes prepared packaged products, such as dietetic sweeteners, liquid sweeteners, granulated flavor mixes which upon reconstitution with water provide non-carbonated drinks, instant pudding mixes, instant coffee and tea, coffee whiteners, malted milk mixes, pet foods, livestock feed, tobacco, and materials for baking applications, such as powdered baking mixes for the preparation of breads, cookies, cakes, pancakes, donuts and the like. Food products also include diet or low-calorie food and beverages containing little or no sucrose. Other examples of food products envisioned in accordance with the present invention are described below and throughout the specification.

In another embodiment, the food products are fruits, vegetables, juices, meat products such as ham, bacon and sausage; egg products, fruit concentrates, gelatins and gelatin-like products such as jams, jellies, preserves, and the like; milk products such as ice cream, sour cream and sherbet; icings, syrups including molasses; corn, wheat, rye, soybean, oat, rice and barley products, nut meats and nut products, cakes, cookies, confectionaries such as candies, gums, fruit flavored drops, and chocolates, creams, icing, ice cream, pies and breads.

In another embodiment, the consumable is a pharmaceutical composition. Preferred compositions are pharmaceutical compositions containing vanillin and/or vanillin beta-D-glucoside and one or more pharmaceutically acceptable excipients. These pharmaceutical compositions can be used to formulate pharmaceutical drugs containing one or more active agents that exert a biological effect. As such, the pharmaceutical composition preferably further include one or more active agents that exert a biological effect. Such active agents include pharmaceutical and biological agents that have an activity. Such active agents are well known in the art. See, e.g., The Physician's Desk Reference. Such compositions can be prepared according to procedures known in the art, for example, as described in Remington's Pharmaceutical Sciences, Mack Publishing Co., Easton, Pa., USA. In one embodiment, such an active agent includes bronchodilators, anorexiants, antihistamines, nutritional supplements, laxatives, analgesics, anesthetics, antacids, H2-receptor antagonists, anticholinergics, antidiarrheals, demulcents, antitussives, antinauseants, antimicrobials, antibacterials, antifungals, antivirals, expectorants, anti-inflammatory agents, antipyretics, and mixtures thereof. In one embodiment, the active agent is an antipyretics or analgesics, e.g., ibuprofen, acetaminophen, or aspirin; laxatives, e.g., phenolphthalein dioctyl sodium sulfosuccinate; appetite depressants, e.g., amphetamines, phenylpropanolamine, phenylpropanolamine hydrochloride, or caffeine; antacidics, e.g., calcium carbonate; antiasthmatics, e.g., theophylline; antidiuretics, e.g., diphenoxylate hydrochloride; agents active against flatulence, e.g., simethecon; migraine agents, e.g., ergotaminetartrate; psychopharmacological agents, e.g., haloperidol; spasmolytics or sedatives, e.g., phenobarbitol; antihyperkinetics, e.g., methyldopa or methylphenidate; tranquilizers, e.g., benzodiazepines, hydroxinmeprobramates or phenothiazines; antihistaminics, e.g., astemizol, chloropheniramine maleate, pyridamine maleate, doxlamine succinate, bromopheniramine maleate, phenyltoloxamine citrate, chlorocyclizine hydrochloride, pheniramine maleate, and phenindamine tartrate; decongestants, e.g., phenylpropanolamine hydrochloride, phenylephrine hydrochloride, pseudoephedrine hydrochloride, pseudoephedrine sulfate, phenylpropanolamine bitartrate, and ephedrine; beta-receptor blockers, e.g., propanolol; agents for alcohol withdrawal, e.g., disulfiram; antitussives, e.g., benzocaine, dextromethorphan, dextromethorphan hydrobromide, noscapine, carbetapentane citrate, and chlophedianol hydrochloride; fluorine supplements, e.g., sodium fluoride; local antibiotics, e.g., tetracycline or cleocine; corticosteroid supplements, e.g., prednisone or prednisolone; agents against goiter formation, e.g., colchicine or allopurinol; antiepileptics, e.g., phenytoine sodium; agents against dehydration, e.g., electrolyte supplements; antiseptics, e.g., cetylpyridinium chloride; NSAIDs, e.g., acetaminophen, ibuprofen, naproxen, or salts thereof; gastrointestinal active agents, e.g., loperamide and famotidine; various alkaloids, e.g., codeine phosphate, codeine sulfate, or morphine; supplements for trace elements, e.g., sodium chloride, zinc chloride, calcium carbonate, magnesium oxide, and other alkali metal salts and alkali earth metal salts; vitamins; ion-exchange resins, e.g., cholestyramine; cholesterol-depressant and lipid-lowering substances; antiarrhythmics, e.g., N-acetylprocainamide; and expectorants, e.g., guaifenesin.

Active substances which have a particularly unpleasant taste include antibacterial agents such as ciprofloxacin, ofloxacin, and pefloxacin; antiepileptics such as zonisamide; macrolide antibiotics such as erythromycin; beta-lactam antibiotics such as penicillins and cephalosporins; psychotropic active substances such as chlorpromazine; active substances such as sulpyrine; and agents active against ulcers, such as cimetidine.

The pharmaceutical compositions of this invention are administered to a subject in any form suitable to achieve their intended purpose. Preferably, however, the composition is one which can be administered buccally or orally. Alternatively, the pharmaceutical composition can be an oral or nasal spray. The subject is any animal, such as a human, although the invention is not intended to be so limited. Other suitable animals include canines, felines, dogs, cats, livestock, horses, cattle, sheep, and the like. A veterinary composition, as used herein, refers to a pharmaceutical composition that suitable for non-human animals. Such veterinary compositions are known in the art.

In another embodiment, the pharmaceutical composition is a liquid dosage form for oral administration, including pharmaceutically acceptable emulsions, solutions, suspensions, syrups, and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

The pharmaceutical composition of the present invention can be in the form of a chewable tablet. Chewable tablets are known in the art. See, e.g., U.S. Pat. Nos. 4,684,534 and 6,060,078, each of which is incorporated by reference in its entirety. Any kind of medicament can be contained in the chewable tablet, preferably a medicament of bitter taste, natural plant extracts or other organic compounds. More preferably, vitamins such as vitamin A, vitamin B, vitamin B1, vitamin B2, vitamin B6, vitamin C, vitamin E and vitamin K; natural plant extracts such as Sohgunjung-tang extracts, Sipchundaebo-tang extracts and *Eleutherococcus senticosus* extracts; organic compounds such as dimenhydrinate, meclazine, acetaminophen, aspirin, phenylpropanolamine, and cetylpyridinium chloride; or gastrointestinal agents such as dried aluminum hydroxide gel, domperidone, soluble azulene, L-glutamine and hydrotalcite can be contained in the core.

The pharmaceutical composition of the present invention can be an orally disintegrating composition. Orally disintegrating tablets are known in the art. See, e.g., U.S. Pat. Nos. 6,368,625 and 6,316,029, each of which is hereby incorporated by reference in its entirety.

The pharmaceutical composition of the present invention can be a solid dosage form, including vanillin or vanillin beta-D-glucoside and a water and/or saliva activated effervescent granule, such as one having a controllable rate of effervescence. The effervescent composition can further comprise a pharmaceutically active compound. Effervescent pharmaceutical compositions are known in the art. See, e.g., U.S. Pat. No. 6,649,186, which is incorporated by reference in its entirety. The effervescent composition can be used in pharmaceutical, veterinary, horticultural, household, food, culinary, pesticidal, agricultural, cosmetic, herbicidal, industrial, cleansing, confectionery and flavoring applications. Formulations incorporating the effervescent composition containing vanillin or vanillin beta-D-glucoside can further include one or more additional adjuvants and/or active ingredients which can be chosen from those known in the art, including flavors, diluents, colors, binders, filler, surfactant, disintegrant, stabilizer, compaction vehicles, and non-effervescent disintegrants.

The pharmaceutical composition can be a film-shaped or wafer-shaped pharmaceutical composition. Such a film-shaped or wafer-shaped pharmaceutical composition can be configured, for example, as quickly disintegrating administration forms, e.g., administration forms disintegrating within a period of 1 second up to 3 minutes, or as slowly disintegrating administration forms, e.g., administration forms disintegrating within a period of 3 to 15 minutes. The indicated disintegration times can be set to the above-mentioned ranges by using, for example, matrix-forming polymers which have different disintegrating, or solubility, characteristics. Thus, by mixing the corresponding polymer components, the disintegration time can be adjusted. In addition, disintegrants are known which "draw" water into the matrix and cause the matrix to burst open from within. As a consequence, certain embodiments of the invention include such disintegrants for the purpose of adjusting the disintegration time.

Suitable are polymers for use in the film-shaped or wafer-shaped pharmaceutical composition include cellulose derivatives, polyvinyl alcohol (e.g. MOWIOL), polyacrylates, polyvinyl pyrrolidone, cellulose ethers, such as ethyl cellulose, as well as polyvinyl alcohol, polyurethane, polymethacrylates, polymethyl methacrylates and derivatives and copolymerizates of the aforementioned polymers.

In certain embodiments, the total thickness of the film-shaped or wafer-shaped pharmaceutical composition according to the invention is preferably 5 µm up to 10 mm, preferably 30 µm to 2 mm, and with particular preference 0.1 mm to 1 mm. The pharmaceutical preparations can be round, oval, elliptic, triangular, quadrangular or polygonal shape, but they can also have any rounded shape.

The pharmaceutical composition of the present invention can be in the form of an aerosol. The aerosol composition can further include a pharmaceutically active agent. Aerosol compositions are known in the art. See, e.g., U.S. Pat. No. 5,011,678, which is hereby incorporated by reference in its entirety. As a nonlimiting example, an aerosol composition according to the present invention can include a medically effective amount of a pharmaceutically active substance, vanillin or vanillin beta-D-glucoside and a biocompatible propellant, such as a (hydro/fluoro)carbon propellant.

In one embodiment of the present invention, the pharmaceutical composition is a nutritional composition. Examples of nutritional compositions having an undesirable taste include, but are not necessarily limited to, enteral nutrition products for treatment of nutritional deficit, trauma, surgery, Crohn's disease, renal disease, hypertension, obesity and the like, to promote athletic performance, muscle enhancement or general well being or inborn errors of metabolism such as phenylketonuria. In particular, such nutritional formulations can contain one or more amino acids which have a bitter or metallic taste or aftertaste. Such amino acids include, but are not limited to, an essential amino acids such as an L isomer of leucine, isoleucine, histidine, lysine, methionine, phenylalanine, threonine, tryptophan, tyrosine or valine.

In one embodiment, the consumable of the present invention is a dental hygienic composition containing vanillin and/or vanillin beta-D-glucoside. Dental hygienic compositions are known in the art and include, but are not necessarily limited to, toothpaste, mouthwash, plaque rinse, dental floss, dental pain relievers (such as ANBESOL), and the like.

In another embodiment, the consumable of the present invention is a cosmetic product containing vanillin and/or vanillin beta-D-glucoside. For example, but not by way of limitation, the cosmetic product can be a face cream, lipstick, lip gloss, and the like. Other suitable compositions of the invention include lip balm, such as CHAPSTICK or BURT'S BEESWAX Lip Balm, further containing vanillin and/or vanillin beta-D-glucoside.

The invention will be further described in the following examples, which do not limit the scope of the invention described in the claims.

Example 1: Yeast Strains with Reduced Alcohol Dehydrogenase/Aldehyde Reductase Activity Yeast strains lacking alcohol dehydrogenase and/or aldehyde reductase were produced in a parent strain of yeast that was capable of producing vanillin/vanillin beta-D-glucoside. The parent strain, EFSC2932, was created by integrating exogenous OMT, UGT and 3DSD genes into the genome of strain EFSC2055 (Genotype: Mata his3D1 leu2D0 met15D0 ura3D0 adh6::LEU2 bgl1::KanMX4 PTPI1::3DSD[AurC]::(HsOMT::MET15[NatMX])::ACAR [HphMX]::UGT7 2E2[HIS3] ECM3::(CorPPTase-Sc-HAP4). Genes encoding OMT, UGT and 3DSD were amplified by polymerase chain reaction (PCR) with gene-specific primers using X7 DNA polymerase. Vectors for chromosomal integration of gene expression were constructed using the uracil-specific excision reagent (USER) cloning method and a vector system adapted from Mikkelsen, et al. ((2012) *Metab. Eng.* 14:104-111). The genes were fused to *Ashbya gossypii* TEF1 promoter and *S. cerevisiae* PGK1 promoter by USER cloning. The resulting constructs were integrated into the following chromosome positions: XII-1 (pTEF1::HsOMT L198Y::pPGK::HsOMTDNA20), XII-2 (pTEF1::HsOMT L198Y+pPGK::UGT72E2) and X-2 (pTEF1::HsOMT L198Y+pPGK::Pa3DSD).

Candidate genes encoding alcohol dehydrogenases or aldehyde reductases were selected and knocked out in various combinations. Cultures of each knockout were analyzed using HPLC-UV to quantify vanillin glucoside/isovanillin glucoside and related products. HPLC analysis was carried out with an AGILENT 1100 series system with binary pump and a Phenomenex Synergi Polar-RP 2.5 u 100 Å 100×2.00 mm column, which separates precursors and Isovanillin and vanillin. A flat gradient was run with water/acetonitrile+0.1% trifluoroacetic acid. A 8.9 minute program+1.1 minute postrun was carried out as presented in Table 2.

TABLE 2

| Time | % Acetonitrile | Flow ml/min. |
|---|---|---|
| 0 | 5 | 0.5 |
| 0.7 | 5 | 0.5 |

TABLE 2-continued

| Time | % Acetonitrile | Flow ml/min. |
|---|---|---|
| 5.7 | 27 | 0.5 |
| 6.2 | 100 | 0.5 |
| 6.6 | 100 | 0.7 |
| 7.8 | 100 | 1.0 |
| 8.1 | 100 | 1.0 |
| 8.6 | 5 | 0.8 |
| 8.9 | 5 | 0.6 |

Vanillin glucoside and isovanillin glucoside were quantified by integrating the area of the HPLC peaks and comparing the same with a standard curve. The combinations of genes disrupted and the resulting effect on vanillyl alcohol production are provided in Table 3.

TABLE 3

| Strain Designation | Gene Disruption 1 | 2 | 3 | Result |
|---|---|---|---|---|
| EFSC2906 | adh6 | adh7 | adh5 | No effect |
| EFSC2907 | adh6 | adh7 | gre3 | No effect |
| EFSC2908 | adh6 | adh7 | ypr127w | No effect |
| EFSC2909 | adh6 | adh7 | ycr102c | No effect |
| EFSC2911 | adh6 | adh7 | ari1 | No effect |
| EFSC2912 | adh6 | adh7 | zta1 | No effect |
| EFSC2913 | adh6 | adh7 | ycr102c | No effect |
| EFSC2929 | adh6 | ari1 | ygl039w | Some effect |
| EFSC2930 | adh6 | adh7 | ylr460c | No effect |
| EFSC2931 | adh6 | adh7 | ygl039w | No effect |
| EFSC2932 | adh6 | adh7 | gre2 | Vanillyl alcohol reduced by 77% |

Figure 2:
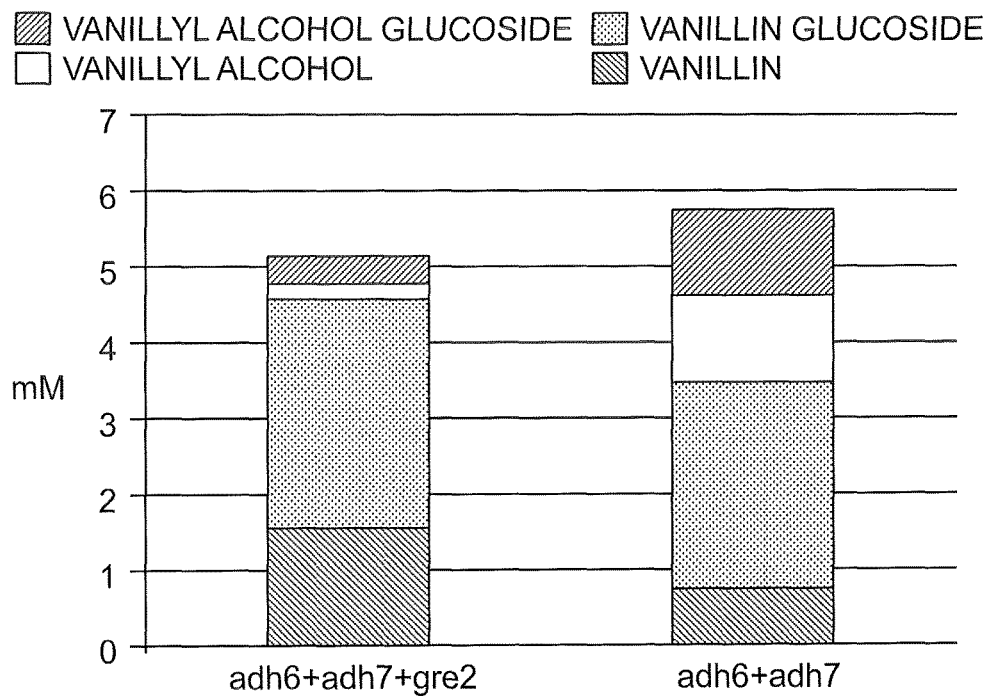
FIG. 2 shows the production of vanillyl alcohol glucoside, vanillyl alcohol, vanillin β-D-glucoside and vanillin in a strain lacking one or more functional alcohol dehydrogenases.

This analysis indicated that, when knocked out, the combination of adh6, adh7 and gre2 provided a 77% decrease in vanillyl alcohol and vanillyl alcohol glucoside production (see FIG. 2).

Figure 3:
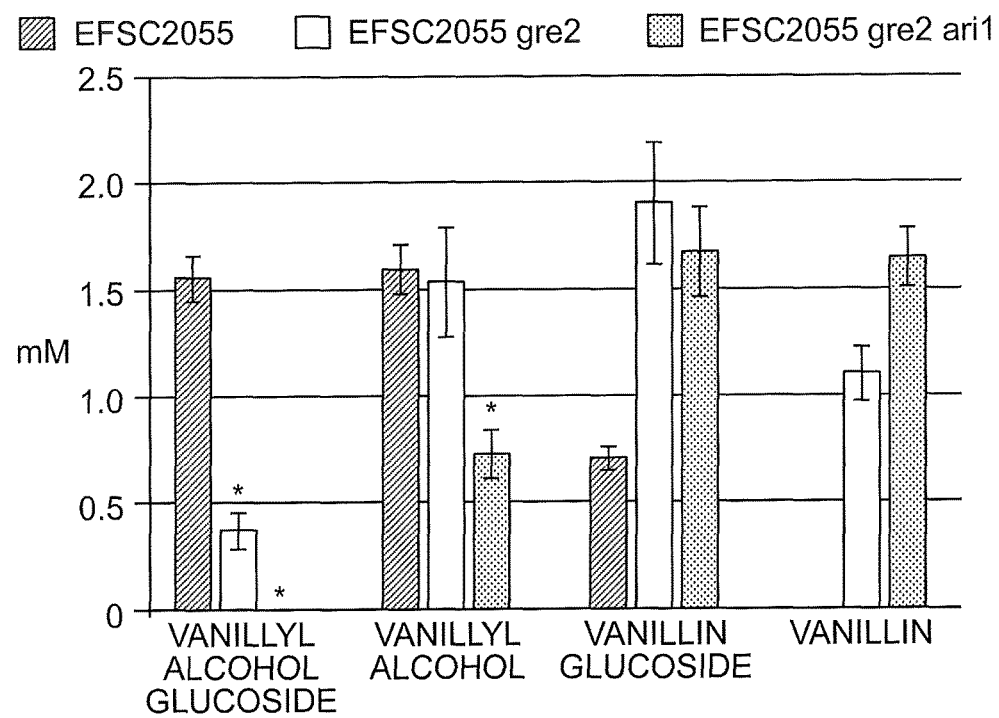
FIG. 3 shows the production of vanillyl alcohol glucoside, vanillyl alcohol, vanillin ρ-D-glucoside and vanillin in a strain lacking gre2 (EFSC2055 gre2) or gre2 and ari1 (EFSC2055 gre2 ari1) as compared to the parental strain EFSC2055. *, p<0.01.

To further analyze the effect of ari1, the ari1 and gre2 genes were deleted in strain EFSC2055 containing adh6 and adh7 gene knockouts. Strain EFSC2055 and the derived single (EFSC2055 gre2) and double mutant (EFSC 2055 gre2 ari1) strains were cultivated for three days in Delft-molasses media (Delft+2% glucose+4% Cane molasses) containing 3 mM of vanillin. EFSC2055 and derived strains encompass the UDP-glycosyltransferase UGT72E2 which is capable of glycosylating vanillin and vanillyl alcohol. Reduction of vanillin to vanillyl alcohol and vanillyl alcohol glycoside was quantified by HPLC-UV. As shown in FIG. 3, the gre2 deletion alone significantly reduced the formation of vanillyl alcohol glycoside from vanillin (t-test, P<0.01). However, the double deletion of both gre2 and ari1 in strain EFSC2055 completely abolished formation of vanillyl alcohol glycoside and significantly reduced formation of vanillyl alcohol (t-test, P<0.01).

Given the observed effect of ari1 and YGL039W deletions, it is contemplated that knocking out one or both of these genes in combination with adh6, adh7 or gre2 (e.g., adh6/adh7/gre2/YGL039W; adh6/adh7/gre2/ari1/YGL039W; adh6/gre2/ari1; adh6/gre2/YGL039W; adh6/gre2/ari1/YGL039W) will also yield a decrease in vanillyl alcohol and vanillyl alcohol glucoside production.

What is claimed is:

1. A recombinant host cell having the following characteristics:
    (a) the recombinant host cell produces vanillin and/or vanillin glycoside; and
    (b) the recombinant host cell has a gene disruption or replacement of a first alcohol dehydrogenase gene and a gene disruption or replacement of:
        (i) two or more second alcohol dehydrogenase genes,
        (ii) one or more aldehyde reductase genes, or
        (iii) a combination of the genes of (i) and (ii).

2. The recombinant host cell of claim 1, wherein the first alcohol dehydrogenase gene is Alcohol Dehydrogenase 6 (ADH6).

3. The recombinant host cell of claim 1, wherein the two or more second alcohol dehydrogenase genes are Alcohol Dehydrogenase 7 (ADH7) and Genes de Respuesta a Estres 2 (GRE2).

4. The recombinant host cell of claim 1, wherein the one or more aldehyde reductase genes are Aldehyde Reductase Intermediate 1 (ARI1) or *Saccharomyces* Aldehyde Reductase YGL039W.

5. The recombinant host cell of claim 1, wherein the recombinant host cell further comprises a nucleic acid encoding an AROM polypeptide, a nucleic acid encoding a catechol-O-methyltransferase (COMT) polypeptide, a nucleic acid encoding a 3-dehydroshikimate dehydratase (3DSD) polypeptide, a nucleic acid encoding an aromatic carboxylic acid reductase (ACAR) polypeptide, a nucleic acid encoding a phosphopantetheine transferase (PPTase) polypeptide, a nucleic acid encoding an uridine 5'-diphosphoglucosyl transferase (UGT) polypeptide and/or a nucleic acid encoding a vanillyl alcohol oxidase (VAO).

6. The recombinant host cell of claim 1, wherein the recombinant host cell is a microorganism.

7. The recombinant host cell of claim 5, wherein the microorganism is *Saccharomyces cerevisiae, Schizosaccharomyces pombe* or *Escherichia coli*.

8. The recombinant host cell of claim 1, wherein the recombinant host cell is a plant cell.

9. The recombinant host cell of claim 8, wherein the plant cell is a *Physcomitrella* cell or tobacco plant cell.

10. A recombinant yeast cell having the following characteristics:
    (a) the recombinant yeast cell produces vanillin and/or vanillin glycoside; and
    (b) the recombinant yeast cell has a gene disruption or replacement of:
        (i) at least three alcohol dehydrogenase genes,
        (ii) at least one aldehyde reductase gene, or
        (iii) at least one alcohol dehydrogenase gene and at least one aldehyde reductase gene.

11. The recombinant yeast cell of claim 10, wherein the alcohol dehydrogenase genes of (i) are Alcohol Dehydrogenase 6 (ADH6), Alcohol Dehydrogenase 7 (ADH7), and Genes de Respuesta a Estres 2 (GRE2); and the alcohol dehydrogenase gene of (iii) is ADH6, ADH7, or GRE2.

12. The recombinant yeast cell of claim 10, wherein the aldehyde reductase gene is Aldehyde Reductase Intermediate 1 (ARI1), or *Saccharomyces* Aldehyde Reductase YGL039W.

13. The recombinant yeast cell of claim 10, wherein the recombinant yeast cell further comprises a nucleic acid encoding an AROM polypeptide, a nucleic acid encoding a catechol-O-methyltransferase (COMT) polypeptide, a nucleic acid encoding a 3-dehydroshikimate dehydratase (3DSD) polypeptide, a nucleic acid encoding an aromatic carboxylic acid reductase (ACAR) polypeptide, a nucleic acid encoding a phosphopantetheine transferase (PPTase) polypeptide, a nucleic acid encoding an uridine 5'-diphosphoglucosyl transferase (UGT) polypeptide and/or a nucleic acid encoding a vanillyl alcohol oxidase (VAO).

14. The recombinant yeast cell of claim 10, wherein the recombinant yeast cell is a member of the genus *Saccharomyces*.

15. The recombinant yeast cell of claim 14, wherein the recombinant yeast cell is *Saccharomyces cerevisiae*.

16. A method for producing vanillin and/or vanillin glycoside comprising:
    (a) providing a recombinant host that produces vanillin and/or vanillin glycoside and has a gene disruption or replacement of:
        (i) at least three a alcohol dehydrogenase genes,
        (ii) at least one aldehyde reductase gene, or
        (iii) at least one alcohol dehydrogenase gene and at least one aldehyde reductase gene;
    (b) cultivating said recombinant host for a time sufficient for said recombinant host to produce vanillin and/or vanillin glycoside; and
    (c) isolating vanillin and/or vanillin glycoside from said recombinant host or from the cultivation supernatant, thereby producing vanillin and/or vanillin glycoside.

17. The method of claim 16, wherein the alcohol dehydrogenase genes of (i) are Alcohol Dehydrogenase 6 (ADH6), Alcohol Dehydrogenase 7 (ADH7), and Genes de Respuesta a Estres 2 (CRE2); and the alcohol dehydrogenase gene of (iii) is ADH6, ADH7 or GRE2.

18. The method of claim 16, wherein the aldehyde reductase gene is Aldehyde Reductase Intermediate 1 (ARI1), or *Saccharomyces* Aldehyde Reductase YGL039W.

19. The method of claim 16, wherein the recombinant host further comprises a nucleic acid encoding an AROM polypeptide, a nucleic acid encoding a catechol-O-methyltransferase (COMT) polypeptide, a nucleic acid encoding a 3-dehydroshikimate dehydratase (3DSD) polypeptide, a nucleic acid encoding an aromatic carboxylic acid reductase (ACAR) polypeptide, a nucleic acid encoding a phosphopantetheine transferase (PPTase) polypeptide, a nucleic acid encoding an uridine 5'-diphosphoglucosyl transferase (UGT) polypeptide and/or a nucleic acid encoding a vanillyl alcohol oxidase (VAO).

20. The method of claim 16, wherein the recombinant host is a microorganism.

21. The method of claim 20, wherein the microorganism is *Saccharomyces cerevisiae, Schizosaccharomyces pombe* or *Escherichia coli*.

22. The method of claim 16, wherein the recombinant host is a plant or plant cell.

23. The method of claim 22, wherein the recombinant host is a *Physcomitrella* plant, a tobacco plant, a *Physcomitrella* plant cell or a tobacco plant cell.

* * * * *

SEQUENCE LISTING

```
<160> NUMBER OF SEQ ID NOS: 24

<210> SEQ ID NO 1
<211> LENGTH: 360
<212> TYPE: PRT
<213> ORGANISM: Saccharomyces cerevisiae

<400> SEQUENCE: 1

Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
                20                  25                  30

Asp His Asp Ile Asp Ile Lys Ile Glu Ala Cys Gly Val Cys Gly Ser
            35                  40                  45

Asp Ile His Cys Ala Ala Gly His Trp Gly Asn Met Lys Met Pro Leu
        50                  55                  60

Val Val Gly His Glu Ile Val Gly Lys Val Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
```

```
                  115                 120                 125
Tyr Val Ser Gln Gly Gly Tyr Ala Asn Tyr Val Arg Val His Glu His
      130                 135                 140

Phe Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255

Ile Asp Phe Asn Ile Met Pro Lys Ala Met Lys Val Gly Gly Arg Ile
            260                 265                 270

Val Ser Ile Ser Ile Pro Glu Gln His Glu Met Leu Ser Leu Lys Pro
        275                 280                 285

Tyr Gly Leu Lys Ala Val Ser Ile Ser Tyr Ser Ala Leu Gly Ser Ile
    290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
            340                 345                 350

Gly Tyr Asp Lys Glu Phe Ser Asp
    355                 360

<210> SEQ ID NO 2
<211> LENGTH: 1083
<212> TYPE: DNA
<213> ORGANISM: Saccharomyces cerevisiae

<400> SEQUENCE: 2
atgtcttatc ctgagaaatt tgaaggtatc gctattcaat cacacgaaga ttggaaaaac      60
ccaaagaaga caaagtatga cccaaaacca ttttacgatc atgacattga cattaagatc     120
gaagcatgtg gtgtctgcgg tagtgatatt cattgtgcag ctggtcattg gggcaatatg     180
aagatgccgc tagtcgttgg tcatgaaatc gttggtaaag ttgtcaagct agggcccaag     240
tcaaacagtg ggttgaaagt cggtcaacgt gttggtgtag gtgctcaagt cttttcatgc     300
ttggaatgtg accgttgtaa gaatgataat gaaccatact gcaccaagtt tgttaccaca     360
tacagtcagc cttatgaaga cggctatgtg tcgcagggtg gctatgcaaa ctacgtcaga     420
gttcatgaac attttgtggt gcctatccca gagaatattc catcacattt ggctgctcca     480
ctattatgtg gtgggttgac tgtgtactct ccattggttc gtaacggttg cggtccaggt     540
aaaaaagttg gtatagttgg tcttggtggt atcggcagta tgggtacatt gatttccaaa     600
gccatggggg cagagactta tgttatttct cgttcttcga gaaaaagaga agatgcaatg     660
aagatgggcg ccgatcacta cattgctaca ttagaagaag gtgattgggg tgaaaagtac     720
```

```
tttgacacct tcgacctgat tgtagtctgt gcttcctccc ttaccgacat tgacttcaac    780
attatgccaa aggctatgaa ggttggtggt agaattgtct caatctctat accagaacaa    840
cacgaaatgt tatcgctaaa gccatatggc ttaaggctg tctccatttc ttacagtgct     900
ttaggttcca tcaaagaatt gaaccaactc ttgaaattag tctctgaaaa agatatcaaa    960
atttgggtgg aaacattacc tgttggtgaa gccggcgtcc atgaagcctt cgaaaggatg   1020
gaaaagggtg acgttagata tagatttacc ttagtcggct acgacaaaga attttcagac   1080
tag                                                                 1083

<210> SEQ ID NO 3
<211> LENGTH: 361
<212> TYPE: PRT
<213> ORGANISM: Saccharomyces cerevisiae

<400> SEQUENCE: 3

Met Leu Tyr Pro Glu Lys Phe Gln Gly Ile Gly Ile Ser Asn Ala Lys
1               5                   10                  15

Asp Trp Lys His Pro Lys Leu Val Ser Phe Asp Pro Lys Pro Phe Gly
            20                  25                  30

Asp His Asp Val Asp Val Glu Ile Glu Ala Cys Gly Ile Cys Gly Ser
        35                  40                  45

Asp Phe His Ile Ala Val Gly Asn Trp Gly Pro Val Pro Glu Asn Gln
    50                  55                  60

Ile Leu Gly His Glu Ile Ile Gly Arg Val Val Lys Val Gly Ser Lys
65                  70                  75                  80

Cys His Thr Gly Val Lys Ile Gly Asp Arg Val Gly Val Gly Ala Gln
                85                  90                  95

Ala Leu Ala Cys Phe Glu Cys Glu Arg Cys Lys Ser Asp Asn Glu Gln
            100                 105                 110

Tyr Cys Thr Asn Asp His Val Leu Thr Met Trp Thr Pro Tyr Lys Asp
        115                 120                 125

Gly Tyr Ile Ser Gln Gly Gly Phe Ala Ser His Val Arg Leu His Glu
    130                 135                 140

His Phe Ala Ile Gln Ile Pro Glu Asn Ile Pro Ser Pro Leu Ala Ala
145                 150                 155                 160

Pro Leu Leu Cys Gly Gly Ile Thr Val Phe Ser Pro Leu Leu Arg Asn
                165                 170                 175

Gly Cys Gly Pro Gly Lys Arg Val Gly Ile Val Gly Ile Gly Gly Ile
            180                 185                 190

Gly His Met Gly Ile Leu Leu Ala Lys Ala Met Gly Ala Glu Val Tyr
        195                 200                 205

Ala Phe Ser Arg Gly His Ser Lys Arg Glu Asp Ser Met Lys Leu Gly
    210                 215                 220

Ala Asp His Tyr Ile Ala Met Leu Glu Asp Lys Gly Trp Thr Glu Gln
225                 230                 235                 240

Tyr Ser Asn Ala Leu Asp Leu Val Val Cys Ser Ser Ser Leu Ser
                245                 250                 255

Lys Val Asn Phe Asp Ser Ile Val Lys Ile Met Lys Ile Gly Gly Ser
            260                 265                 270

Ile Val Ser Ile Ala Ala Pro Glu Val Asn Glu Lys Leu Val Leu Lys
        275                 280                 285

Pro Leu Gly Leu Met Gly Val Ser Ile Ser Ser Ala Ile Gly Ser
    290                 295                 300
```

```
Arg Lys Glu Ile Glu Gln Leu Leu Lys Leu Val Ser Glu Lys Asn Val
305                 310                 315                 320

Lys Ile Trp Val Glu Lys Leu Pro Ile Ser Glu Glu Gly Val Ser His
                325                 330                 335

Ala Phe Thr Arg Met Glu Ser Gly Asp Val Lys Tyr Arg Phe Thr Leu
            340                 345                 350

Val Asp Tyr Asp Lys Lys Phe His Lys
            355                 360

<210> SEQ ID NO 4
<211> LENGTH: 1086
<212> TYPE: DNA
<213> ORGANISM: Saccharomyces cerevisiae

<400> SEQUENCE: 4
atgctttacc cagaaaaatt tcagggcatc ggtatttcca acgcaaagga ttggaagcat        60
cctaaattag tgagttttga cccaaaaccc tttggcgatc atgacgttga tgttgaaatt       120
gaagcctgtg gtatctgcgg atctgatttt catatagccg ttggtaattg gggtccagtc       180
ccagaaaatc aaatccttgg acatgaaata attggccgcg tggtgaaggt tggatccaag       240
tgccacactg gggtaaaaat cggtgaccgt gttggtgttg gtgcccaagc cttggcgtgt       300
tttgagtgtg aacgttgcaa aagtgacaac gagcaatact gtaccaatga ccacgttttg       360
actatgtgga ctccttacaa ggacggctac atttcacaag gaggctttgc ctcccacgtg       420
aggcttcatg aacactttgc tattcaaata ccagaaaata ttccaagtcc gctagccgct       480
ccattattgt gtggtggtat tacagttttc tctccactac taagaaatgg ctgtggtcca       540
ggtaagaggg taggtattgt tggcatcggt ggtattgggc atatggggat tctgttggct       600
aaagctatgg gagccgaggt ttatgcgttt tcgcgaggcc actccaagcg ggaggattct       660
atgaaactcg gtgctgatca ctatattgct atgttggagg ataaaggctg acagaacaa       720 tactctaacg ctttggacct tcttgtcgtt tgctcatcat ctttgtcgaa agttaatttt       780
gacagtatcg ttaagattat gaagattgga ggctccatcg tttcaattgc tgctcctgaa       840
gttaatgaaa agcttgtttt aaaaccgttg ggcctaatgg gagtatcaat ctcaagcagt       900
gctatcggat ctaggaagga aatcgaacaa ctattgaaat tagtttccga aaagaatgtc       960
aaaatatggg tggaaaaact tccgatcagc gaagaaggcg tcagccatgc ctttacaagg      1020
atggaaagcg gagacgtcaa atacagattt actttggtcg attatgataa gaaattccat      1080
aaatag                                                                1086

<210> SEQ ID NO 5
<211> LENGTH: 341
<212> TYPE: PRT
<213> ORGANISM: Saccharomyces cerevisiae

<400> SEQUENCE: 5

Met Ser Val Phe Val Ser Gly Ala Asn Gly Phe Ile Ala Gln His Ile
1               5                   10                  15

Val Asp Leu Leu Leu Lys Glu Asp Tyr Lys Val Ile Gly Ser Ala Arg
            20                  25                  30

Ser Gln Glu Lys Ala Glu Asn Leu Thr Glu Ala Phe Gly Asn Asn Pro
        35                  40                  45

Lys Phe Ser Met Glu Val Val Pro Asp Ile Ser Lys Leu Asp Ala Phe
    50                  55                  60

Asp His Val Phe Gln Lys His Gly Lys Asp Ile Lys Ile Val Leu His
```

```
                65                  70                  75                  80
        Thr Ala Ser Pro Phe Cys Phe Asp Ile Thr Asp Ser Glu Arg Asp Leu
                            85                  90                  95

Leu Ile Pro Ala Val Asn Gly Val Lys Gly Ile Leu His Ser Ile Lys
                        100                 105                 110

Lys Tyr Ala Ala Asp Ser Val Glu Arg Val Val Leu Thr Ser Ser Tyr
                    115                 120                 125

Ala Ala Val Phe Asp Met Ala Lys Glu Asn Asp Lys Ser Leu Thr Phe
                130                 135                 140

Asn Glu Glu Ser Trp Asn Pro Ala Thr Trp Glu Ser Cys Gln Ser Asp
        145                 150                 155                 160

Pro Val Asn Ala Tyr Cys Gly Ser Lys Lys Phe Ala Glu Lys Ala Ala
                        165                 170                 175

Trp Glu Phe Leu Glu Glu Asn Arg Asp Ser Val Lys Phe Glu Leu Thr
                    180                 185                 190

Ala Val Asn Pro Val Tyr Val Phe Gly Pro Gln Met Phe Asp Lys Asp
                195                 200                 205

Val Lys Lys His Leu Asn Thr Ser Cys Glu Leu Val Asn Ser Leu Met
                210                 215                 220

His Leu Ser Pro Glu Asp Lys Ile Pro Glu Leu Phe Gly Gly Tyr Ile
        225                 230                 235                 240

Asp Val Arg Asp Val Ala Lys Ala His Leu Val Ala Phe Gln Lys Arg
                        245                 250                 255

Glu Thr Ile Gly Gln Arg Leu Ile Val Ser Glu Ala Arg Phe Thr Met
                    260                 265                 270

Gln Asp Val Leu Asp Ile Leu Asn Glu Asp Phe Pro Val Leu Lys Gly
                275                 280                 285

Asn Ile Pro Val Gly Lys Pro Gly Ser Gly Ala Thr His Asn Thr Leu
                290                 295                 300

Gly Ala Thr Leu Asp Asn Lys Lys Ser Lys Lys Leu Leu Gly Phe Lys
        305                 310                 315                 320

Phe Arg Asn Leu Lys Glu Thr Ile Asp Asp Thr Ala Ser Gln Ile Leu
                        325                 330                 335

Lys Phe Glu Gly Arg
                    340

<210> SEQ ID NO 6
<211> LENGTH: 1029
<212> TYPE: DNA
<213> ORGANISM: Saccharomyces cerevisiae

<400> SEQUENCE: 6
atgtcagttt tcgtttcagg tgctaacggg ttcattgccc aacacattgt cgatctcctg      60
ttgaaggaag actataaggt catcggttct gccagaagtc aagaaaaggc cgagaattta     120
acggaggcct tggtaacaa  cccaaaattc tccatggaag ttgtcccaga catatctaag     180
ctggacgcat tgaccatgt  tttccaaaag cacggcaagg atatcaagat agttctacat     240
acggcctctc cattctgctt tgatatcact gacagtgaac gcgatttatt aattcctgct     300
gtgaacggtg ttaagggaat tctccactca attaaaaaat acgccgctga ttctgtagaa     360
cgtgtagttc tcacctcttc ttatgcagct gtgttcgata tggcaaaaga aaacgataag     420
tctttaacat ttaacgaaga atcctggaac ccagctacct gggagagttg ccaaagtgac     480
ccagttaacg cctactgtgg ttctaagaag tttgctgaaa aagcagcttg ggaatttcta     540
```

-continued

```
gaggagaata gagactctgt aaaattcgaa ttaactgccg ttaacccagt ttacgttttt      600
ggtccgcaaa tgtttgacaa agatgtgaaa aaacacttga acacatcttg cgaactcgtc      660
aacagcttga tgcatttatc accagaggac aagataccgg aactatttgg tggatacatt      720
gatgttcgtg atgttgcaaa ggctcattta gttgccttcc aaaagaggga acaattggt       780 caaagactaa tcgtatcgga ggccagattt actatgcagg atgttctcga tatccttaac      840
gaagacttcc ctgttctaaa aggcaatatt ccagtgggga accaggttc tggtgctacc       900 cataacaccc ttggtgctac tcttgataat aaaaagagta agaaattgtt aggtttcaag      960
ttcaggaact tgaaagagac cattgacgac actgcctccc aaattttaaa atttgagggc     1020
agaatataa                                                             1029
```

<210> SEQ ID NO 7
<211> LENGTH: 344
<212> TYPE: PRT
<213> ORGANISM: Saccharomyces cerevisiae

<400> SEQUENCE: 7

```
Met Ser Asn Thr Val Leu Val Ser Gly Ala Ser Gly Phe Ile Ala Leu
1               5                   10                  15

His Ile Leu Ser Gln Leu Leu Lys Gln Asp Tyr Lys Val Ile Gly Thr
            20                  25                  30

Val Arg Ser His Glu Lys Glu Ala Lys Leu Leu Arg Gln Phe Gln His
        35                  40                  45

Asn Pro Asn Leu Thr Leu Glu Ile Val Pro Asp Ile Ser His Pro Asn
    50                  55                  60

Ala Phe Asp Lys Val Leu Gln Lys Arg Gly Arg Glu Ile Arg Tyr Val
65                  70                  75                  80

Leu His Thr Ala Ser Pro Phe His Tyr Asp Thr Thr Glu Tyr Glu Lys
                85                  90                  95

Asp Leu Leu Ile Pro Ala Leu Glu Gly Thr Lys Asn Ile Leu Asn Ser
            100                 105                 110

Ile Lys Lys Tyr Ala Ala Asp Thr Val Glu Arg Val Val Val Thr Ser
        115                 120                 125

Ser Cys Thr Ala Ile Ile Thr Leu Ala Lys Met Asp Asp Pro Ser Val
    130                 135                 140

Val Phe Thr Glu Glu Ser Trp Asn Glu Ala Thr Trp Glu Ser Cys Gln
145                 150                 155                 160

Ile Asp Gly Ile Asn Ala Tyr Phe Ala Ser Lys Lys Phe Ala Glu Lys
                165                 170                 175

Ala Ala Trp Glu Phe Thr Lys Glu Asn Glu Asp His Ile Lys Phe Lys
            180                 185                 190

Leu Thr Thr Val Asn Pro Ser Leu Phe Gly Pro Gln Leu Phe Asp
        195                 200                 205

Glu Asp Val His Gly His Leu Asn Thr Ser Cys Glu Met Ile Asn Gly
    210                 215                 220

Leu Ile His Thr Pro Val Asn Ala Ser Val Pro Asp Phe His Ser Ile
225                 230                 235                 240

Phe Ile Asp Val Arg Asp Val Ala Leu Ala His Leu Tyr Ala Phe Gln
                245                 250                 255

Lys Glu Asn Thr Ala Gly Lys Arg Leu Val Val Thr Asn Gly Lys Phe
            260                 265                 270

Gly Asn Gln Asp Ile Leu Asp Ile Leu Asn Glu Asp Phe Pro Gln Leu
        275                 280                 285
```

Arg Gly Leu Ile Pro Leu Gly Lys Pro Gly Thr Gly Asp Gln Val Ile
            290                 295                 300

Asp Arg Gly Ser Thr Thr Asp Asn Ser Ala Thr Arg Lys Ile Leu Gly
305                 310                 315                 320

Phe Glu Phe Arg Ser Leu His Glu Ser Val His Asp Thr Ala Ala Gln
                325                 330                 335

Ile Leu Lys Lys Gln Asn Arg Leu
            340

<210> SEQ ID NO 8
<211> LENGTH: 1035
<212> TYPE: DNA
<213> ORGANISM: Saccharomyces cerevisiae

<400> SEQUENCE: 8

```
atgtctaata cagttctagt ttctggcgct tcaggttta ttgccttgca tatcctgtca      60
caattgttaa acaagatta taaggttatt ggaactgtga atcccatga aaaagaagca     120
aaattgctaa acaatttca acataaccct aatttaactt tagaaattgt tccggacatt     180
tctcatccaa atgctttcga taaggttctg cagaaacgtg acgtgagat taggtatgtt     240
ctacacacgg cctctccttt tcattatgat actaccgaat atgaaaaga cttattgatt     300
cccgcgttag aaggtacaaa aaacatccta aattctatca gaaatatgc agcagacact     360
gtagagcgtg ttgttgtgac ttcttcttgt actgctatta taaccttgc aaagatggac     420
gatcccagtg tggtttttac agaagagagt tggaacgaag caacctggga aagctgtcaa     480
attgatggga taaatgctta ctttgcatcc aagaagtttg ctgaaaaggc tgcctgggag     540
ttcacaaaag agaatgaaga tcacatcaaa tcaaactaa caacagtcaa cccttctctt     600
cttttggtc ctcaactttt cgatgaagat gtgcatggcc atttgaatac ttcttgcgaa     660
atgatcaatg gcctaattca taccccagta atgccagtg ttcctgattt tcattccatt     720
tttattgatg taagggatgt ggccctagct catctgtatg ctttccagaa ggaaaatacc     780
gcgggtaaaa gattagtggt aactaacggt aaatttggaa accaagatat cctggatatt     840
ttgaacgaag atttttccaca attaagaggt ctcattcctt tgggtaagcc tggcacaggt     900
gatcaagtca ttgaccgcgg ttcaactaca gataatagtg caacgaggaa aatacttggc     960
tttgagttca agtttaca cgaaagtgtc catgatactg ctgcccaaat tttgaagaag    1020
cagaacagat tatga                                                    1035
```

<210> SEQ ID NO 9
<211> LENGTH: 347
<212> TYPE: PRT
<213> ORGANISM: Saccharomyces cerevisiae

<400> SEQUENCE: 9

Met Thr Thr Asp Thr Thr Val Phe Val Ser Gly Ala Thr Gly Phe Ile
1               5                  10                  15

Ala Leu His Ile Met Asn Asp Leu Leu Lys Ala Gly Tyr Thr Val Ile
            20                  25                  30

Gly Ser Gly Arg Ser Gln Glu Lys Asn Asp Gly Leu Leu Lys Lys Phe
        35                  40                  45

Asn Asn Asn Pro Lys Leu Ser Met Glu Ile Val Glu Asp Ile Ala Ala
    50                  55                  60

Pro Asn Ala Phe Asp Glu Val Phe Lys Lys His Gly Lys Glu Ile Lys
65                  70                  75                  80

```
Ile Val Leu His Thr Ala Ser Pro Phe His Phe Glu Thr Thr Asn Phe
                85                  90                  95
Glu Lys Asp Leu Leu Thr Pro Ala Val Asn Gly Thr Lys Ser Ile Leu
            100                 105                 110
Glu Ala Ile Lys Lys Tyr Ala Ala Asp Thr Val Glu Lys Val Ile Val
        115                 120                 125
Thr Ser Ser Thr Ala Ala Leu Val Thr Pro Thr Asp Met Asn Lys Gly
    130                 135                 140
Asp Leu Val Ile Thr Glu Glu Ser Trp Asn Lys Asp Thr Trp Asp Ser
145                 150                 155                 160
Cys Gln Ala Asn Ala Val Ala Ala Tyr Cys Gly Ser Lys Lys Phe Ala
                165                 170                 175
Glu Lys Thr Ala Trp Glu Phe Leu Lys Glu Asn Lys Ser Ser Val Lys
            180                 185                 190
Phe Thr Leu Ser Thr Ile Asn Pro Gly Phe Val Phe Gly Pro Gln Met
        195                 200                 205
Phe Ala Asp Ser Leu Lys His Gly Ile Asn Thr Ser Ser Gly Ile Val
    210                 215                 220
Ser Glu Leu Ile His Ser Lys Val Gly Gly Glu Phe Tyr Asn Tyr Cys
225                 230                 235                 240
Gly Pro Phe Ile Asp Val Arg Asp Val Ser Lys Ala His Leu Val Ala
                245                 250                 255
Ile Glu Lys Pro Glu Cys Thr Gly Gln Arg Leu Val Leu Ser Glu Gly
            260                 265                 270
Leu Phe Cys Cys Gln Glu Ile Val Asp Ile Leu Asn Glu Glu Phe Pro
        275                 280                 285
Gln Leu Lys Gly Lys Ile Ala Thr Gly Glu Pro Ala Thr Gly Pro Ser
    290                 295                 300
Phe Leu Glu Lys Asn Ser Cys Lys Phe Asp Asn Ser Lys Thr Lys Lys
305                 310                 315                 320
Leu Leu Gly Phe Gln Phe Tyr Asn Leu Lys Asp Cys Ile Val Asp Thr
                325                 330                 335
Ala Ala Gln Met Leu Glu Val Gln Asn Glu Ala
            340                 345

<210> SEQ ID NO 10
<211> LENGTH: 1044
<212> TYPE: DNA
<213> ORGANISM: Saccharomyces cerevisiae

<400> SEQUENCE: 10
atgactactg ataccactgt tttcgtttct ggcgcaaccg gtttcattgc tctacacatt      60
atgaacgatc tgttgaaagc tggctataca gtcatcggct caggtagatc tcaagaaaaa     120
aatgatggct tgctcaaaaa atttaataac aatcccaaac tatcgatgga aattgtggaa     180
gatattgctg ctccaaacgc ctttgatgaa gttttcaaaa acatggtaa ggaaattaag      240 attgtgctac acactgcctc cccattccat tttgaaacta ccaattttga aaaggattta     300
ctaacccctg cagtgaacgg tacaaaatct atcttggaag cgattaaaaa atatgctgca     360
gacactgttg aaaaagttat tgttacttcg tctactgctg ctctggtgac acctacagac     420
atgaacaaag agatttggt gatcacggag gagagttgga ataaggatac atgggacagt     480
tgtcaagcca acgccgttgc cgcatattgt ggctcgaaaa agtttgctga aaaaactgct     540
tgggaatttc ttaaagaaaa caagtctagt gtcaaattca cactatccac tatcaatccg     600
```

```
ggattcgttt ttggtcctca aatgtttgca gattcgctaa aacatggcat aaataccctcc      660 tcagggatcg tatctgagtt aattcattcc aaggtaggtg gagaatttta taattactgt      720
ggcccattta ttgacgtgcg tgacgtttct aaagcccacc tagttgcaat tgaaaaacca      780
gaatgtaccg gccaaagatt agtattgagt gaaggtttat tctgctgtca agaaatcgtt      840
gacatcttga acgaggaatt ccctcaatta aagggcaaga tagctacagg tgaacctgcg      900
accggtccaa gctttttaga aaaaactct tgcaagtttg acaattctaa gacaaaaaaa       960
ctactgggat tccagtttta caatttaaag gattgcatag ttgacaccgc ggcgcaaatg     1020
ttagaagttc aaaatgaagc ctaa                                            1044
```

<210> SEQ ID NO 11
<211> LENGTH: 348
<212> TYPE: PRT
<213> ORGANISM: Saccharomyces cerevisiae

<400> SEQUENCE: 11

```
Met Thr Thr Glu Lys Thr Val Val Phe Val Ser Gly Ala Thr Gly Phe
  1               5                  10                  15

Ile Ala Leu His Val Val Asp Asp Leu Leu Lys Thr Gly Tyr Lys Val
             20                  25                  30

Ile Gly Ser Gly Arg Ser Gln Glu Lys Asn Asp Gly Leu Leu Lys Lys
         35                  40                  45

Phe Lys Ser Asn Pro Asn Leu Ser Met Glu Ile Val Glu Asp Ile Ala
     50                  55                  60

Ala Pro Asn Ala Phe Asp Lys Val Phe Gln Lys His Gly Lys Glu Ile
 65                  70                  75                  80

Lys Val Val Leu His Ile Ala Ser Pro Val His Phe Asn Thr Thr Asp
                 85                  90                  95

Phe Glu Lys Asp Leu Leu Ile Pro Ala Val Asn Gly Thr Lys Ser Ile
            100                 105                 110

Leu Glu Ala Ile Lys Asn Tyr Ala Ala Asp Thr Val Glu Lys Val Val
        115                 120                 125

Ile Thr Ser Ser Val Ala Ala Leu Ala Ser Pro Gly Asp Met Lys Asp
    130                 135                 140

Thr Ser Phe Val Val Asn Glu Glu Ser Trp Asn Lys Asp Thr Trp Glu
145                 150                 155                 160

Ser Cys Gln Ala Asn Ala Val Ser Ala Tyr Cys Gly Ser Lys Lys Phe
                165                 170                 175

Ala Glu Lys Thr Ala Trp Asp Phe Leu Glu Glu Asn Gln Ser Ser Ile
            180                 185                 190

Lys Phe Thr Leu Ser Thr Ile Asn Pro Gly Phe Val Phe Gly Pro Gln
        195                 200                 205

Leu Phe Ala Asp Ser Leu Arg Asn Gly Ile Asn Ser Ser Ser Ala Ile
    210                 215                 220

Ile Ala Asn Leu Val Ser Tyr Lys Leu Gly Asp Asn Phe Tyr Asn Tyr
225                 230                 235                 240

Ser Gly Pro Phe Ile Asp Val Arg Asp Val Ser Lys Ala His Leu Leu
                245                 250                 255

Ala Phe Glu Lys Pro Glu Cys Ala Gly Gln Arg Leu Phe Leu Cys Glu
            260                 265                 270

Asp Met Phe Cys Ser Gln Glu Ala Leu Asp Ile Leu Asn Glu Glu Phe
        275                 280                 285
```

Pro Gln Leu Lys Gly Lys Ile Ala Thr Gly Glu Pro Gly Ser Gly Ser
          290                 295                 300

Thr Phe Leu Thr Lys Asn Cys Cys Lys Cys Asp Asn Arg Lys Thr Lys
305                 310                 315                 320

Asn Leu Leu Gly Phe Gln Phe Asn Lys Phe Arg Asp Cys Ile Val Asp
                325                 330                 335

Thr Ala Ser Gln Leu Leu Glu Val Gln Ser Lys Ser
                340                 345

<210> SEQ ID NO 12
<211> LENGTH: 1047
<212> TYPE: DNA
<213> ORGANISM: Saccharomyces cerevisiae

<400> SEQUENCE: 12

| | | | | | |
|---|---|---|---|---|---|
| atgactactg | aaaaaaccgt | tgttttttgtt | tctggtgcta | ctggtttcat | tgctctacac | 60 |
| gtagtggacg | atttattaaa | aactggttac | aaggtcatcg | gttcgggtag | gtcccaagaa | 120 |
| aagaatgatg | gattgctgaa | aaatttaag | agcaatccca | accttcaat | ggagattgtc | 180 |
| gaagacattg | ctgctccaaa | cgcttttgac | aaagttttc | aaaagcacgg | caaagagatc | 240 |
| aaggttgtct | tgcacatagc | ttctccggtt | cacttcaaca | ccactgattt | cgaaaaggat | 300 |
| ctgctaattc | ctgctgtgaa | tggtaccaag | tccattctag | aagcaatcaa | aaattatgcc | 360 |
| gcagacacag | tcgaaaaagt | cgttattact | tcttctgttg | ctgcccttgc | atctcccgga | 420 |
| gatatgaagg | acactagttt | cgttgtcaat | gaggaaagtt | ggaacaaaga | tacttgggaa | 480 |
| agttgtcaag | ctaacgcggt | ttccgcatac | tgtggttcca | agaaatttgc | tgaaaaaact | 540 |
| gcttgggatt | tctctcgagga | aaaccaatca | agcatcaaat | ttacgctatc | aaccatcaac | 600 |
| ccaggatttg | tttttggccc | tcagctattt | gccgactctc | ttagaaatgg | aataaatagc | 660 |
| tcttcagcca | ttattgccaa | tttggttagt | tataaattag | gcgacaattt | ttataattac | 720 |
| agtggtccttt | ttattgacgt | tcgcgatgtt | tcaaaagctc | atttacttgc | atttgagaaa | 780 |
| cccgaatgcg | ctggccaaag | actattctta | tgtgaagata | tgttttgctc | tcaagaagcg | 840 |
| ctggatatct | tgaatgagga | atttccacag | ttaaaaggca | agatagcaac | tggcgaacct | 900 |
| ggtagcggct | caaccttttt | gacaaaaaac | tgctgcaagt | gcgacaaccg | caaaaccaaa | 960 |
| aatttattag | gattccaatt | taataagttc | agagattgca | ttgtcgatac | tgcctcgcaa | 1020 |
| ttactagaag | ttcaaagtaa | aagctaa | | | | 1047 |

<210> SEQ ID NO 13
<211> LENGTH: 336
<212> TYPE: PRT
<213> ORGANISM: Schizosaccharomyces pombe

<400> SEQUENCE: 13

Met Ser Gly Lys Leu Val Leu Val Thr Gly Val Thr Gly Phe Ile Gly
1               5                   10                  15

Ala His Val Ala Glu Gln Leu Leu Gln Ala Gly Tyr Arg Val Arg Gly
                20                  25                  30

Thr Val Arg Ser Met Glu Lys Ala Asp Glu Leu Ile Arg Leu Asn Pro
            35                  40                  45

Gly Leu Lys Asp Lys Ile Glu Phe Val Ile Val Lys Asp Val Ser Ala
        50                  55                  60

Ser Asn Ala Phe Asp Gly Val Leu Lys Asp Val Glu Leu Ile Cys His
65                  70                  75                  80

```
Ile Ala Ser Pro Phe Phe Val Glu Asn Val Thr Asp Asn Lys Ser Gln
                85                  90                  95
Leu Leu Asp Pro Ala Val Lys Gly Thr Leu Gly Ile Leu Glu Ala Ala
            100                 105                 110
Gln Gly Val Lys Ser Ile Lys Arg Ile Val Ile Thr Ser Ser Phe Ala
        115                 120                 125
Ala Val Gly Asn Phe Gln Ile Asp Pro His Asn Asn Lys Val Tyr Thr
    130                 135                 140
Glu Lys Asp Trp Asn Pro Ile Thr Tyr Glu Ala Leu Thr Thr Asp
145                 150                 155                 160
Asn Gly Ile Val Ala Tyr Cys Ala Ser Lys Lys Leu Ala Glu Ala
                165                 170                 175
Ala Arg Glu Tyr Val Lys Glu Lys Pro Ser Tyr Asp Ile Cys Thr
            180                 185                 190
Ile Asn Pro Pro Tyr Val Tyr Gly Pro Pro Ile His Pro Met Lys Asn
        195                 200                 205
Met Asp Ser Leu Asn Thr Ser Asn Gln Ile Phe Trp Lys Leu Ile Asp
    210                 215                 220
Gly Ser Lys Glu Ala Thr Pro Phe Tyr Tyr Tyr Val Asp Val Arg
225                 230                 235                 240
Asp Val Ala Ala His Val Phe Ala Leu Glu Asn Ala Lys Leu Ser
                245                 250                 255
Asn Gly Arg Met Leu Val Ser Lys Gly Val Phe Thr Thr Gly Asp Ile
            260                 265                 270
Cys Lys Val Leu Arg Lys Glu Phe Pro Asn Lys Ser Asp Val Ile Ala
        275                 280                 285
Glu Pro Val Asp Ile Thr Val Asp Pro Ser Phe Phe Lys Leu Asp Asn
    290                 295                 300
Ser Phe Ser Lys Ser Leu Gly Phe Lys Tyr His Ser Asp Glu Glu Cys
305                 310                 315                 320
Tyr Val Asp Thr Ala Lys Lys Leu Trp Glu Arg Ala Glu Glu Phe Lys
                325                 330                 335

<210> SEQ ID NO 14
<211> LENGTH: 1759
<212> TYPE: DNA
<213> ORGANISM: Schizosaccharomyces pombe

<400> SEQUENCE: 14
tccataaatc tgaaaactgc tttttatatc ttttaccat gaatagaata gctgtatgcc      60
aaagcgggat actaaattta cacaaccatt tattttcatt ttctttctaa tttgtattaa     120
caaaactttt attgctcaga agcaatagct gaccattgtt tacatcccta cttcttact     180 aaatttccgt attacgaaac tctcctgtat tcaacaagtt ttgtgagact tttactataa     240
tgcgtaagaa atggcagaac gaaaacttga gaaagtcaag ttatccattt cacgtcatgt     300
tatagcccat taataatatt atatttgatt actaaaaaaa tgggaacaat cggatgcgca     360
acttccgaag aaaaatatgg aacaaatttt tcgttgccta ctcattttct tatatattac     420
aaggaaagtc tacttccatt gtcaacaagt gatatttcag gtataatcac ttatattttt     480
tagaacaaac acaaaacctt caaagatgag tggaaaattg gtccttgtta ctggtgttac     540 aggattatt ggagcccacg tcgctgagca gctcctgcaa gccggctacc gtgtgcgtgg      600
tacggtgaga agcatggaaa aggcagacga gcttattaga ctcaatcccg gattaaagga     660
taaaattgag tttgtaatcg tcaaggatgt ctctgcttct aacgcttttg acggtgtttt     720
```

-continued

```
gaaagatgtg gaattgattt gtcatatagc atcaccattc tttgtggaaa acgttactga      780
caacaaatcc caacttttgg accctgccgt gaagggtact ctcggcattt tagaggctgc      840
tcaaggcgta agagtatta agcgcattgt tattacttca tcttttgccg cagtgggcaa       900
tttccaaatc gaccctcata acaataaggt gtatactgag aaggattgga atcccattac      960
ctatgaggag gcattgacca ctgataatgg cattgtagca tactgtgctt cgaagaaact     1020
cgccgaagag gctgctcgag agtatgtaaa ggaaaagaag ccttcttatg atatttgtac     1080
gatcaatcct ccttatgtgt atggtccacc aattcaccct atgaaaaata tggactcttt     1140
aaatacctcc aatcaaatat tttggaaatt aatcgatgga tcgaaggaag ccactccatt     1200
ttattattac tatgttgatg tccgtgatgt agctgctgct cacgttttg ccttgagaa      1260 cgccaagttg tctaacggcc gtatgcttgt ctccaagggt gtattcacta ctggtgatat     1320
ttgcaaggtc cttcgcaaag aattccccaa caagtccgat gttattgccg agcccgtcga     1380
tataactgtg gatcccagtt tcttcaagtt agacaactca ttttccaagt ctcttggatt     1440
caaatatcat tccgacgagg aatgctatgt tgacactgct aagaagttat gggaacgtgc     1500
tgaggagttt aaataaaatg tttacaaacg ttgggttgag cattcttttg ttacgaattc     1560 attttgctc cttatttatt tcacgatttc ttctttcaat ttatatcgct acgacatata     1620
tagactttag acatattaaa ttattagaat ttcattgcat ttagataaaa gacttttttc     1680
gatagtgctt gtcggtacac tttgttgtat acaattttt caatattttg aaatttttta     1740
ctctatcaat cgatttgcg                                                  1759
```

<210> SEQ ID NO 15
<211> LENGTH: 375
<212> TYPE: PRT
<213> ORGANISM: Arabidopsis thaliana

<400> SEQUENCE: 15

```
Met Val Asp Gln Asn Arg Ala Phe Gly Trp Ala Ala Asn Asp Glu Ser
1               5                   10                  15

Gly Val Leu Ser Pro Phe His Phe Ser Arg Arg Glu Asn Gly Glu Asn
            20                  25                  30

Asp Val Thr Val Lys Ile Leu Phe Cys Gly Val Cys His Ser Asp Leu
        35                  40                  45

His Thr Ile Lys Asn His Trp Gly Phe Ser Arg Tyr Pro Ile Ile Pro
    50                  55                  60

Gly His Glu Ile Val Gly Ile Ala Thr Lys Val Gly Lys Asn Val Thr
65                  70                  75                  80

Lys Phe Lys Glu Gly Asp Arg Val Gly Val Gly Val Ile Ile Gly Ser
                85                  90                  95

Cys Gln Ser Cys Glu Ser Cys Asn Gln Asp Leu Glu Asn Tyr Cys Pro
            100                 105                 110

Lys Val Val Phe Thr Tyr Asn Ser Arg Ser Ser Asp Gly Thr Arg Asn
        115                 120                 125

Gln Gly Gly Tyr Ser Asp Val Ile Val Val Asp His Arg Phe Val Leu
    130                 135                 140

Ser Ile Pro Asp Gly Leu Pro Ser Asp Ser Gly Ala Pro Leu Leu Cys
145                 150                 155                 160

Ala Gly Ile Thr Val Tyr Ser Pro Met Lys Tyr Tyr Gly Met Thr Lys
                165                 170                 175

Glu Ser Gly Lys Arg Leu Gly Val Asn Gly Leu Gly Gly Leu Gly His
```

```
            180                 185                 190
Ile Ala Val Lys Ile Gly Lys Ala Phe Gly Leu Arg Val Thr Val Ile
            195                 200                 205

Ser Arg Ser Ser Glu Lys Glu Arg Glu Ala Ile Asp Arg Leu Gly Ala
            210                 215                 220

Asp Ser Phe Leu Val Thr Thr Asp Ser Gln Lys Met Lys Glu Ala Val
225                 230                 235                 240

Gly Thr Met Asp Phe Ile Ile Asp Thr Val Ser Ala Glu His Ala Leu
                    245                 250                 255

Leu Pro Leu Phe Ser Leu Leu Lys Val Ser Gly Lys Leu Val Ala Leu
                260                 265                 270

Gly Leu Leu Glu Lys Pro Leu Asp Leu Pro Ile Phe Pro Leu Val Leu
            275                 280                 285

Gly Arg Lys Met Val Gly Gly Ser Gln Ile Gly Gly Met Lys Glu Thr
            290                 295                 300

Gln Glu Met Leu Glu Phe Cys Ala Lys His Lys Ile Val Ser Asp Ile
305                 310                 315                 320

Glu Leu Ile Lys Met Ser Asp Ile Asn Ser Ala Met Asp Arg Leu Val
                    325                 330                 335

Lys Ser Asp Val Arg Tyr Arg Phe Val Ile Asp Val Ala Asn Ser Leu
                340                 345                 350

Leu Pro Glu Ser Ser Ala Glu Ile Leu Thr Glu His Val Asp His Gly
            355                 360                 365

Val Ser Ile Thr Ser Arg Phe
            370                 375

<210> SEQ ID NO 16
<211> LENGTH: 1128
<212> TYPE: DNA
<213> ORGANISM: Arabidopsis thaliana

<400> SEQUENCE: 16
atggtagatc aaaatagagc atttggttgg gcggccaacg acgaatcggg cgtcctctct      60
ccatttcatt tctctagaag agaaaatggt gagaacgatg taacagtgaa gatcttgttc     120
tgtggtgttt gtcactctga tcttcatacc atcaagaacc attggggatt ctctcgttac     180
cccattattc ccgggcatga aatcgttgga atagcaacaa aagttgggaa gaatgtgaca     240
aagtttaaag aaggagaccg agtaggagta ggcgtaataa tcggttcatg ccaatcatgt     300
gaatcatgta accaagactt agaaaactat tgtcctaaag tcgttttcac atacaactct     360
cgttcctctg acggaaccag aaaccaaggt ggttattccg acgtaattgt tgtcgatcac     420
cgctttgtcc taagcattcc cgacggttta ccaagcgatt caggcgcgcc gctgctctgt     480
gctggaatca ctgtgtacag tcccatgaag tattatggca tgactaaaga atcagggaaa     540
cgtttaggtg tgaatggact tggtggactt ggtcatatcg ctgttaagat tggtaaagcc     600
tttggtttaa gagttactgt gattagtagg tcatcagaga aagagagaga agcaattgat     660
cgactcggtg ctgattcgtt tcttgttaca acggattctc aaaagatgaa ggaagcagtt     720
ggaactatgg atttcattat cgatacggta tcagcagaac atgctctatt accttttgttt     780 agtttgctta aagtgagtgg aaagcttgtg ctttaggct tgctggagaa gccactcgac     840
ctgccaattt tccctctagt tctcggaagg aaaatggtgg aggaagtca gattggaggg     900 atgaaggaga cacaagagat gcttgagttc tgtgccaagc ataaaatcgt ttcggatatt     960
gagctcataa agatgagtga tatcaactct gcgatggacc gtttggttaa atctgatgtc    1020
```

```
aggtaccggt tcgtgatcga tgtggccaac tctttactcc ctgagtcgtc agctgagatt    1080
ttaacggagc atgtcgacca tggagtctcg atcacgtcta gattctga                1128
```

<210> SEQ ID NO 17
<211> LENGTH: 360
<212> TYPE: PRT
<213> ORGANISM: Arabidopsis thaliana

<400> SEQUENCE: 17

```
Met Ala Lys Ser Pro Glu Thr Glu His Pro Asn Lys Val Phe Gly Trp
1               5                   10                  15

Gly Ala Arg Asp Lys Ser Gly Val Leu Ser Pro Phe His Phe Ser Arg
            20                  25                  30

Arg Asp Asn Gly Glu Asn Asp Val Thr Val Lys Ile Leu Phe Cys Gly
        35                  40                  45

Val Cys His Thr Asp Leu His Thr Ile Lys Asn Asp Trp Gly Tyr Ser
    50                  55                  60

Tyr Tyr Pro Val Val Pro Gly His Glu Ile Val Gly Ile Ala Thr Lys
65                  70                  75                  80

Val Gly Lys Asn Val Thr Lys Phe Lys Glu Gly Asp Arg Val Gly Val
                85                  90                  95

Gly Val Ile Ser Gly Ser Cys Gln Ser Cys Glu Ser Cys Asp Gln Asp
            100                 105                 110

Leu Glu Asn Tyr Cys Pro Gln Met Ser Phe Thr Tyr Asn Ala Ile Gly
        115                 120                 125

Ser Asp Gly Thr Lys Asn Tyr Gly Gly Tyr Ser Glu Asn Ile Val Val
    130                 135                 140

Asp Gln Arg Phe Val Leu Arg Phe Pro Glu Asn Leu Pro Ser Asp Ser
145                 150                 155                 160

Gly Ala Pro Leu Leu Cys Ala Gly Ile Thr Val Tyr Ser Pro Met Lys
                165                 170                 175

Tyr Tyr Gly Met Thr Glu Ala Gly Lys His Leu Gly Val Ala Gly Leu
            180                 185                 190

Gly Gly Leu Gly His Val Ala Val Lys Ile Gly Lys Ala Phe Gly Leu
        195                 200                 205

Lys Val Thr Val Ile Ser Ser Ser Thr Lys Ala Glu Glu Ala Ile
    210                 215                 220

Asn His Leu Gly Ala Asp Ser Phe Leu Val Thr Thr Asp Pro Gln Lys
225                 230                 235                 240

Met Lys Ala Ala Ile Gly Thr Met Asp Tyr Ile Ile Asp Thr Ile Ser
                245                 250                 255

Ala Val His Ala Leu Tyr Pro Leu Leu Gly Leu Leu Lys Val Asn Gly
            260                 265                 270

Lys Leu Ile Ala Leu Gly Leu Pro Glu Lys Pro Leu Glu Leu Pro Met
        275                 280                 285

Phe Pro Leu Val Leu Gly Arg Lys Met Val Gly Gly Ser Asp Val Gly
    290                 295                 300

Gly Met Lys Glu Thr Gln Glu Met Leu Asp Phe Cys Ala Lys His Asn
305                 310                 315                 320

Ile Thr Ala Asp Ile Glu Leu Ile Lys Met Asp Glu Ile Asn Thr Ala
                325                 330                 335

Met Glu Arg Leu Ala Lys Ser Asp Val Arg Tyr Arg Phe Val Ile Asp
            340                 345                 350
```

Val Ala Asn Ser Leu Ser Pro Pro
       355                 360

<210> SEQ ID NO 18
<211> LENGTH: 1744
<212> TYPE: DNA
<213> ORGANISM: Arabidopsis thaliana

<400> SEQUENCE: 18

| | | |
|---|---|---|
| acacaacata aacccaatct ctcactcaga ctaagacaga gtcagaaaca atggcgaaat | 60 |
| ctccagaaac agagcatccg aacaaagtct ttggttgggg tgctagagac aaatccggtg | 120 |
| ttctctctcc ttttcacttc tctagaagag acaatggtga aaatgatgtg acagtgaaga | 180 |
| tcttgttctg tggagtttgc cacactgatt tacacaccat caaaaacgac tggggatact | 240 |
| cgtattaccc agtagttcca ggcatgaaa tcgttgggat cgctacaaaa gttggtaaga | 300 |
| acgtgactaa attcaaagaa ggagatcgtg tcggagtagg agtgatcagt ggctcgtgcc | 360 |
| aatcttgcga tcttgtgac caagatcttg aaaactactg tcctcaaatg tctttcacat | 420 |
| acaatgcgat tggatccgat ggaaccaaga attacggtgg ctattcggag aacattgtgg | 480 |
| ttgatcaacg gtttgttttg cggtttccgg agaatttacc gagcgattcg ggtgcgccgt | 540 |
| tgctgtgtgc tggaatcact gtgtatagtc aatgaagta ttatggtatg actgaggcag | 600 |
| ggaagcattt aggggttgct ggacttggtg ggcttggtca tgttgctgtt aagattggta | 660 |
| aagcttttgg tttgaaagtt actgtcatta gttcttcttc tacgaaagca gaggaagcca | 720 |
| ttaatcatct tggtgctgat tcgtttcttg tcacaactga tcctcagaaa atgaaggctg | 780 |
| caattggaac aatggactac attatcgata cgatatcagc agtacatgct ctgtatccgt | 840 |
| tgctcggttt actcaaagtc aacggaaagc tcattgcttt aggcttacct gagaagcctc | 900 |
| tcgagctacc aatgttccct cttgttctcg aaggaaaat ggttggagga agtgacgtgg | 960 |
| gagggatgaa ggagacacaa gagatgcttg atttctgcgc taagcacaac attacagctg | 1020 |
| atattgaatt gattaagatg gatgagatta acactgcgat ggagaggctt gctaagtctg | 1080 |
| atgttaggta caggttcgtg atcgacgtgg ctaactcctt gagccctcca tgaatgatcc | 1140 |
| ggatctaaga attgagcatt gaggaggctt taaatctatg tcataatctt ggtgtttgtt | 1200 |
| tgtgtctctc gagttatctt cgttttctgc tttcggtttg agaatcggtt tcttctcaga | 1260 |
| caagttacct tatttcgttg ttttcttctc atgttctgtt tcctgagaga aactcttttct | 1320 |
| gattccagat aagactttga tccattttca gtttgctaat aatataaaga tgggtctaaa | 1380 |
| acctaaacag ctttaaactc tttatgattt taaagaatct caatatgcag atcattggaa | 1440 |
| ttgtgatcat ttaaacatga gcgtttatta attgatatga agttactat caaactatt | 1500 |
| tgggagacga agccggagaa gagtcgccgg agtttggatt ctgacaaaag ccacgaagga | 1560 |
| cattagcttc ctcaggcgta aatccgagag aagtgagcat cgccggccag caattggtgg | 1620 |
| tgatgatgtc tacggattcg caacaactaa caccaagttt tgtttcaccg ttgaggaaga | 1680 |
| agagaacgat ctcgttggtg catgatttca gctcgtataa tgcgttccag cattccatca | 1740 |
| gtcc | 1744 |

<210> SEQ ID NO 19
<211> LENGTH: 376
<212> TYPE: PRT
<213> ORGANISM: Arabidopsis thaliana

<400> SEQUENCE: 19

```
Met Val Asp Gln Asn Lys Ala Phe Gly Trp Ala Ala Asn Asp Glu Ser
1               5                   10                  15

Gly Val Leu Ser Pro Phe His Phe Ser Arg Arg Glu Asn Gly Glu Asn
            20                  25                  30

Asp Val Thr Val Lys Ile Leu Phe Cys Gly Val Cys His Ser Asp Leu
        35                  40                  45

His Thr Ile Lys Asn His Trp Gly Phe Ser Arg Tyr Pro Ile Ile Pro
    50                  55                  60

Gly His Glu Ile Val Gly Ile Ala Thr Lys Val Gly Lys Asn Val Thr
65                  70                  75                  80

Lys Phe Lys Glu Gly Asp Arg Val Gly Val Gly Val Ile Ile Gly Ser
                85                  90                  95

Cys Gln Ser Cys Glu Ser Cys Asn Gln Asp Leu Glu Asn Tyr Cys Pro
                100                 105                 110

Lys Val Phe Thr Tyr Asn Ser Arg Ser Ser Asp Gly Thr Ser Arg
            115                 120                 125

Asn Gln Gly Gly Tyr Ser Asp Val Ile Val Asp His Arg Phe Val
    130                 135                 140

Leu Ser Ile Pro Asp Gly Leu Pro Ser Asp Ser Gly Ala Pro Leu Leu
145                 150                 155                 160

Cys Ala Gly Ile Thr Val Tyr Ser Pro Met Lys Tyr Tyr Gly Met Thr
                165                 170                 175

Lys Glu Ser Gly Lys Arg Leu Gly Val Asn Gly Leu Gly Leu Gly
            180                 185                 190

His Ile Ala Val Lys Ile Gly Lys Ala Phe Gly Leu Arg Val Thr Val
    195                 200                 205

Ile Ser Arg Ser Ser Glu Lys Glu Arg Glu Ala Ile Asp Arg Leu Gly
    210                 215                 220

Ala Asp Ser Phe Leu Val Thr Thr Asp Ser Gln Lys Met Lys Glu Ala
225                 230                 235                 240

Val Gly Thr Met Asp Phe Ile Ile Asp Thr Val Ser Ala Glu His Ala
                245                 250                 255

Leu Leu Pro Leu Phe Ser Leu Leu Lys Val Asn Gly Lys Leu Val Ala
                260                 265                 270

Leu Gly Leu Pro Glu Lys Pro Leu Asp Leu Pro Ile Phe Ser Leu Val
            275                 280                 285

Leu Gly Arg Lys Met Val Gly Gly Ser Gln Ile Gly Gly Met Lys Glu
            290                 295                 300

Thr Gln Glu Met Leu Glu Phe Cys Ala Lys His Lys Ile Val Ser Asp
305                 310                 315                 320

Ile Glu Leu Ile Lys Met Ser Asp Ile Asn Ser Ala Met Asp Arg Leu
                325                 330                 335

Ala Lys Ser Asp Val Arg Tyr Arg Phe Val Ile Asp Val Ala Asn Ser
            340                 345                 350

Leu Leu Pro Glu Ser Ser Ala Glu Ile Leu Thr Glu Gln Val Asp His
            355                 360                 365

Gly Val Ser Ile Thr Ser Arg Phe
    370                 375

<210> SEQ ID NO 20
<211> LENGTH: 1141
<212> TYPE: DNA
<213> ORGANISM: Arabidopsis thaliana

<400> SEQUENCE: 20
```

-continued

```
agaaacaaat atggtagatc aaaataaagc atttggttgg gcggccaacg acgaatcggg    60
cgtcctctct ccatttcatt tctctagaag agaaaatggt gagaacgatg taacagtgaa   120
gatcttgttc tgtggtgttt gtcactctga tcttcatacc atcaagaacc attggggatt   180
ctctcgttac cccattattc ccgggcatga atcgttgga atagcaacaa aagttgggaa    240
gaatgtgaca agtttaaag aaggagaccg agtaggagta ggcgtaataa tcggttcatg    300
ccaatcatgt gaatcatgta accaagactt agaaaactat tgtcctaaag tcgttttcac   360
atacaactct cgttcctctg acggaaccag cagaaaccaa ggtggttatt ccgacgtaat   420
tgttgtcgat caccgctttg tcctaagcat tcccgatggt ttaccaagcg attcaggcgc   480
gccgctgctc tgtgctggaa tcactgtgta cagtcccatg aagtattatg catgactaa    540 agaatcaggg aaacgtttag gtgtgaatgg acttggtgga cttggtcata tcgctgttaa   600
gattggtaaa gcctttggtt taagagttac tgtgattagt aggtcatcag aaaagagag    660 agaagcaatt gatcggcttg gtgctgattc gtttcttgtt acaacggatt ctcaaaagat   720
gaaggaagcg gttggaacta tggatttcat tatcgatacg gtatcagcag aacatgctct   780
attaccgttg tttagtttgc ttaaagtgaa tggaaagctt gtggctttag cttaccgga    840 gaagccactc gacctgccaa ttttctctct agttctcgga aggaaaatgg tgggaggaag   900
tcagattgga gggatgaagg agacacaaga gatgcttgag ttctgtgcca agcataaaat   960
cgtttcggat attgagctca taaagatgag tgatatcaac tctgcgatgg accgtttggc  1020
taaatctgat gtcaggtacc ggttcgtgat cgatgtggcc aactctttac tccctgagtc  1080
gtcagctgag attttaacgg agcaggtgga ccatggagtc tcgatcacgt ctagattctg  1140
a                                                                  1141
```

<210> SEQ ID NO 21
<211> LENGTH: 325
<212> TYPE: PRT
<213> ORGANISM: Arabidopsis thaliana

<400> SEQUENCE: 21

```
Met Ser Ser Glu Glu Lys Thr Val Cys Val Thr Gly Ala Ser Gly
1               5                  10                  15

Tyr Ile Ala Ser Trp Ile Val Lys Leu Leu Leu Arg Gly Tyr Thr
            20                  25                  30

Val Lys Ala Ser Val Arg Asp Pro Asn Asp Pro Arg Lys Thr Glu His
        35                  40                  45

Leu Leu Ala Leu Glu Gly Ala Glu Glu Arg Leu Lys Leu Phe Lys Ala
    50                  55                  60

Asn Leu Leu Glu Glu Gly Ser Phe Asp Ser Ala Ile Asp Gly Cys Glu
65                  70                  75                  80

Gly Val Phe His Thr Ala Ser Pro Phe Tyr His Asp Val Lys Asp Pro
                85                  90                  95

Gln Ala Glu Leu Leu Asp Pro Ala Val Lys Gly Thr Ile Asn Val Leu
            100                 105                 110

Ser Ser Cys Leu Lys Thr Ser Ser Val Lys Arg Val Val Leu Thr Ser
        115                 120                 125

Ser Ile Ala Ala Val Ala Phe Asn Gly Met Pro Arg Thr Pro Glu Thr
    130                 135                 140

Ile Val Asp Glu Thr Trp Phe Ala Asp Pro Asp Tyr Cys Arg Ala Ser
145                 150                 155                 160
```

Lys Leu Trp Tyr Val Leu Ser Lys Thr Leu Ala Glu Asn Ala Ala Trp
                165                 170                 175

Lys Phe Ala Lys Glu Asn Asn Leu Gln Leu Val Ser Ile Asn Pro Ala
            180                 185                 190

Met Val Ile Gly Pro Leu Leu Gln Pro Thr Leu Asn Thr Ser Ala Ala
        195                 200                 205

Ala Val Leu Ser Leu Ile Lys Gly Ala Gln Thr Phe Pro Asn Ala Thr
    210                 215                 220

Phe Gly Trp Val Asn Val Lys Asp Val Ala Asn Ala His Ile Gln Ala
225                 230                 235                 240

Phe Glu Asn Pro Asp Ala Asp Gly Arg Tyr Cys Leu Val Glu Arg Val
                245                 250                 255

Ala His Tyr Ser Glu Val Val Asn Ile Leu His Asp Leu Tyr Pro Asp
            260                 265                 270

Phe Gln Leu Pro Glu Lys Cys Ala Asp Glu Lys Ile Tyr Ile Pro Thr
        275                 280                 285

Tyr Lys Val Ser Lys Glu Lys Ala Glu Ser Leu Gly Val Glu Phe Val
    290                 295                 300

Pro Leu Glu Val Ser Ile Lys Glu Thr Val Glu Ser Leu Arg Asp Lys
305                 310                 315                 320

Gly Phe Ile Arg Phe
            325

<210> SEQ ID NO 22
<211> LENGTH: 978
<212> TYPE: DNA
<213> ORGANISM: Arabidopsis thaliana

<400> SEQUENCE: 22
atgagcagcg aagaagagaa gacagtgtgt gtgacaggag cttcaggtta cattgcttca      60
tggatcgtta agcttcttct tctccgtggt tacaccgtta aagcctctgt tcgtgatcca     120
aatgatccaa ggaaaacaga gcatttgctt gcattggaag gagcagagga aaggcttaaa     180
ttgttcaaag caaacttgtt agaagaaggc tctttcgatt cagcaatcga tggttgcgaa     240
ggagttttcc acaccgcatc gccattctat catgacgtca aggaccctca ggctgagtta     300
cttgatccgg cagtgaaagg aacaatcaat gttctaagct cttgtttgaa gacttcctcg     360
gttaagagag tcgtcttaac ctcatcgata gcagctgttg ctttcaatgg aatgcctcga     420
acacccgaaa ccatagttga cgaaacttgg ttcgccgatc ctgactattg cagagcttcc     480
aagctatggt atgtactctc gaagacatta gctgaaaacg cagcgtggaa attcgcaaaa     540
gagaacaatt tacagctggt ttcgataaat ccggctatgg tgattggtcc tctcttacag     600
ccaacgctaa acactagtgc tgctgcagta ctaagcttga tcaaaggagc acaaacgttt     660
cctaatgcga cgttcgggtg ggttaacgtt aaagatgtag cgaacgctca tattcaagcg     720
tttgagaatc cagatgctga tgggagatac tgtttagtgg agagagttgc tcattactct     780
gaagttgtta acattttgca tgatctttac cctgattttc aactccctga agtgtgca      840 gatgaaaaga tatatattcc aacatataaa gtgtctaaag agaaagcaga gtctcttggg     900
gttgagtttg tgccattgga agttagcatt aaagagactg tagagagctt gagagataaa     960
gggttcatca gatttttga                                                 978

<210> SEQ ID NO 23
<211> LENGTH: 326
<212> TYPE: PRT

<213> ORGANISM: Arabidopsis thaliana

<400> SEQUENCE: 23

Met Ala Asn Ser Gly Glu Gly Lys Val Val Cys Val Thr Gly Ala Ser
1               5                   10                  15

Gly Tyr Ile Ala Ser Trp Leu Val Lys Phe Leu Leu Ser Arg Gly Tyr
            20                  25                  30

Thr Val Lys Ala Ser Val Arg Asp Pro Ser Asp Pro Lys Lys Thr Gln
        35                  40                  45

His Leu Val Ser Leu Glu Gly Ala Lys Glu Arg Leu His Leu Phe Lys
    50                  55                  60

Ala Asp Leu Leu Glu Gln Gly Ser Phe Asp Ser Ala Ile Asp Gly Cys
65                  70                  75                  80

His Gly Val Phe His Thr Ala Ser Pro Phe Phe Asn Asp Ala Lys Asp
                85                  90                  95

Pro Gln Ala Glu Leu Ile Asp Pro Ala Val Lys Gly Thr Leu Asn Val
            100                 105                 110

Leu Asn Ser Cys Ala Lys Ala Ser Val Lys Arg Val Val Val Thr
            115                 120                 125

Ser Ser Met Ala Ala Val Gly Tyr Asn Gly Lys Pro Arg Thr Pro Asp
130                 135                 140

Val Thr Val Asp Glu Thr Trp Phe Ser Asp Pro Glu Leu Cys Glu Ala
145                 150                 155                 160

Ser Lys Met Trp Tyr Val Leu Ser Lys Thr Leu Ala Glu Asp Ala Ala
                165                 170                 175

Trp Lys Leu Ala Lys Glu Lys Gly Leu Asp Ile Val Thr Ile Asn Pro
            180                 185                 190

Ala Met Val Ile Gly Pro Leu Leu Gln Pro Thr Leu Asn Thr Ser Ala
        195                 200                 205

Ala Ala Ile Leu Asn Leu Ile Asn Gly Ala Lys Thr Phe Pro Asn Leu
    210                 215                 220

Ser Phe Gly Trp Val Asn Val Lys Asp Val Ala Asn Ala His Ile Gln
225                 230                 235                 240

Ala Phe Glu Val Pro Ser Ala Asn Gly Arg Tyr Cys Leu Val Glu Arg
                245                 250                 255

Val Val His Ser Glu Ile Val Asn Ile Leu Arg Glu Leu Tyr Pro
            260                 265                 270

Asn Leu Pro Leu Pro Glu Arg Cys Val Asp Glu Asn Pro Tyr Val Pro
        275                 280                 285

Thr Tyr Gln Val Ser Lys Asp Lys Thr Arg Ser Leu Gly Ile Asp Tyr
    290                 295                 300

Ile Pro Leu Lys Val Ser Ile Lys Glu Thr Val Glu Ser Leu Lys Glu
305                 310                 315                 320

Lys Gly Phe Ala Gln Phe
                325

<210> SEQ ID NO 24
<211> LENGTH: 1273
<212> TYPE: DNA
<213> ORGANISM: Arabidopsis thaliana

<400> SEQUENCE: 24
caaatatacg cattcgtcat ttggtccctc cacttagaga gaagcagaca gaacataact    60
aaaatcgaga aaaatggcaa acagtggtga aggtaaagtg gtgtgtgtaa caggagcctc   120

-continued

```
cggttacatc gcctcatggc tcgtcaagtt cctacttagc cgtggctaca ctgttaaggc      180
ctccgtccgt gatcccagtg atccgaaaaa gacacaacac ttagtttcac tagaaggtgc      240
aaaggaaaga cttcacttgt tcaaagcaga ccttttggaa caaggttctt tcgactctgc      300
tattgatggt tgccatggag ttttccacac tgcttctcca tttttttaatg atgccaaaga    360 cccacaggct gaacttattg atcctgcggt caaggggacg cttaacgttt tgaattcgtg      420
cgccaaagcc tcttcggtta agagggttgt tgtaacctcc tccatggctg ccgttggtta      480
caatggaaaa ccacgcacac ctgatgttac cgtcgatgaa acttggttct ctgatcctga      540
gctttgcgag gcctccaaga tgtggtatgt tctatccaag actttggcgg aagatgcagc      600
ttggaaactc gctaaagaga aaggcttaga cattgttact attaacccgg ctatggtgat      660
cggtcctctc ctacagccaa ctctgaacac gagtgctgct gctatattaa acttaatcaa      720
tggtgcaaag actttcccaa acttgagttt cggatgggtt aatgtaaaag acgtagccaa      780
tgcgcacatc caagcatttg aggtcccttc agctaatggg cgttattgtt tggtcgagcg      840
tgtcgttcac cactccgaga ttgttaacat tctacgtgag ctttacccaa atctcccact      900
acctgaaagg tgtgtggacg agaatcccta cgtgccaacg tatcaagtgt ccaaggataa      960
aacgaggagc cttggcatag actacatacc cttgaaggtt agcatcaagg agaccgtcga    1020
gtccttgaag gaaaaaggtt tcgcacagtt ctgagaaagc atttgagcca atggatttaa    1080
tccagattag ataaagtatt tggaagacta tttcagaaat aatatttgga acatgtcaat    1140
gttctcaagg agatattagt atgttcttgt gtactttatt gttgttccat caaatgagtt    1200
acttttcctt ttatttcttg ttagtaagat atcaaataag aattcgagtc aagtgagcat    1260
ctttacactg atg                                                       1273
```